(12) United States Patent
Olroyd et al.

(10) Patent No.: US 8,506,532 B2
(45) Date of Patent: Aug. 13, 2013

(54) SYSTEM INCLUDING ACCESS PORT AND APPLICATOR TOOL

(75) Inventors: Craig Olroyd, Santa Barbara, CA (US); Christopher Mudd, Goleta, CA (US); Ahmet Tezel, Goleta, CA (US); Kris Turner, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 395 days.

(21) Appl. No.: 12/772,039

(22) Filed: Apr. 30, 2010

(65) Prior Publication Data

US 2011/0054407 A1 Mar. 3, 2011

Related U.S. Application Data

(60) Provisional application No. 61/263,869, filed on Aug. 26, 2009, provisional application No. 61/237,641, filed on Aug. 27, 2009.

(51) Int. Cl.
*A61M 5/32* (2006.01)

(52) U.S. Cl.
USPC .......................................................... 604/174

(58) Field of Classification Search
USPC .......................................................... 604/174
See application file for complete search history.

(56) References Cited

U.S. PATENT DOCUMENTS

| | | | |
|---|---|---|---|
| 2,163,048 A | 6/1939 | McKee | |
| 2,737,954 A * | 3/1956 | Knapp | .......................... 606/146 |
| 3,587,115 A | 6/1971 | Shiley | |
| 3,596,660 A | 8/1971 | Melone | |
| 3,667,081 A | 6/1972 | Burger | |
| 3,688,764 A | 9/1972 | Reed | |
| 3,731,352 A | 5/1973 | Okamoto et al. | |
| 3,840,018 A | 10/1974 | Heifetz | |
| 3,958,562 A | 5/1976 | Hakim et al. | |
| 3,971,376 A | 7/1976 | Wichterle | |
| 4,019,499 A | 4/1977 | Fitzgerald | |
| 4,118,805 A | 10/1978 | Reimels | |
| 4,151,835 A | 5/1979 | Showell et al. | |
| 4,161,943 A | 7/1979 | Nogier | |
| 4,164,943 A | 8/1979 | Hill et al. | |
| 4,190,040 A | 2/1980 | Schulte | |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS http://en.wikipedia.org/wiki/Injection_molding.*

(Continued)

*Primary Examiner* — Theodore J Stigell
*Assistant Examiner* — Diva K Chander
(74) *Attorney, Agent, or Firm* — Stephen Donovan; Debra Condino

(57) ABSTRACT

The present invention provides a system for attaching a fluid access port to a patient. The system generally comprises an implantable access port and a tool for attaching an access port to a patient. The implantable access port may include a plurality of anchor assemblies composed of two different materials. In addition, a mesh member may be attached to the base of the access port to facilitate implantation of the access port into a patient's body. The tool may have a rotatable actuator head, and may engage the access port in various orientations.

38 Claims, 31 Drawing Sheets

(56) References Cited

U.S. PATENT DOCUMENTS

| | | |
|---|---|---|
| 4,233,992 A | 11/1980 | Bisping |
| 4,265,252 A | 5/1981 | Chubbuck et al. |
| 4,413,985 A | 11/1983 | Wellner |
| 4,474,572 A | 10/1984 | McNaughton et al. |
| 4,502,335 A | 3/1985 | Wamstad et al. |
| 4,543,088 A | 9/1985 | Bootman et al. |
| 4,557,722 A | 12/1985 | Harris |
| 4,569,675 A | 2/1986 | Prosl et al. |
| 4,588,394 A | 5/1986 | Schulte et al. |
| 4,592,339 A | 6/1986 | Kuzmak et al. |
| 4,592,355 A | 6/1986 | Antebi |
| 4,634,427 A | 1/1987 | Hannula et al. |
| 4,655,765 A | 4/1987 | Swift |
| 4,673,394 A | 6/1987 | Fenton, Jr. et al. |
| 4,692,146 A | 9/1987 | Hilger |
| 4,696,288 A | 9/1987 | Kuzmak et al. |
| 4,704,103 A | 11/1987 | Stober et al. |
| 4,710,174 A | 12/1987 | Moden et al. |
| 4,738,657 A | 4/1988 | Hancock et al. |
| 4,767,410 A | 8/1988 | Moden et al. |
| 4,772,270 A | 9/1988 | Wiita et al. |
| 4,778,452 A | 10/1988 | Moden et al. |
| 4,781,680 A | 11/1988 | Redmond et al. |
| 4,796,641 A | 1/1989 | Mills et al. |
| 4,802,885 A | 2/1989 | Weeks et al. |
| 4,832,054 A | 5/1989 | Bark |
| 4,840,615 A | 6/1989 | Hancock et al. |
| 4,850,227 A | 7/1989 | Luettgen et al. |
| 4,858,623 A | 8/1989 | Bradshaw et al. |
| 4,861,341 A | 8/1989 | Woodburn |
| 4,881,939 A | 11/1989 | Newman |
| 4,886,501 A | 12/1989 | Johnston et al. |
| 4,902,278 A | 2/1990 | Maget et al. |
| 4,904,241 A | 2/1990 | Bark |
| 4,913,702 A | 4/1990 | Yum et al. |
| 4,915,690 A | 4/1990 | Cone et al. |
| 4,929,230 A | 5/1990 | Pfleger |
| 4,929,236 A | 5/1990 | Sampson |
| 4,966,588 A | 10/1990 | Rayman et al. |
| 4,967,755 A | 11/1990 | Pohndorf |
| 4,978,338 A | 12/1990 | Melsky et al. |
| 5,006,115 A | 4/1991 | McDonald |
| 5,013,298 A | 5/1991 | Moden et al. |
| 5,026,344 A | 6/1991 | Dijkstra et al. |
| 5,041,098 A | 8/1991 | Loiterman et al. |
| 5,045,060 A | 9/1991 | Melsky et al. |
| 5,074,868 A | 12/1991 | Kuzmak |
| 5,090,954 A | 2/1992 | Geary |
| 5,092,897 A | 3/1992 | Forte |
| 5,094,244 A | 3/1992 | Callahan et al. |
| 5,108,377 A | 4/1992 | Cone et al. |
| 5,125,408 A | 6/1992 | Basser |
| 5,133,753 A | 7/1992 | Bark et al. |
| 5,137,529 A | 8/1992 | Watson et al. |
| 5,147,483 A | 9/1992 | Melsky et al. |
| 5,152,747 A | 10/1992 | Olivier |
| 5,167,638 A | 12/1992 | Felix et al. |
| 5,185,003 A | 2/1993 | Brethauer |
| 5,207,644 A | 5/1993 | Strecker |
| 5,213,574 A | 5/1993 | Tucker |
| 5,226,429 A | 7/1993 | Kuzmak |
| 5,226,894 A | 7/1993 | Haber et al. |
| 5,250,026 A | 10/1993 | Ehrlich et al. |
| 5,273,537 A | 12/1993 | Haskvitz et al. |
| 5,281,205 A | 1/1994 | McPherson |
| 5,284,479 A | 2/1994 | de Jong |
| 5,318,545 A | 6/1994 | Tucker |
| 5,336,194 A | 8/1994 | Polaschegg et al. |
| 5,337,747 A | 8/1994 | Neftel |
| 5,360,407 A | 11/1994 | Leonard et al. |
| 5,368,040 A | 11/1994 | Carney |
| 5,387,192 A | 2/1995 | Glantz et al. |
| 5,449,368 A | 9/1995 | Kuzmak |
| 5,476,460 A | 12/1995 | Montalvo |
| 5,514,174 A | 5/1996 | Heil, Jr. et al. |
| 5,540,648 A | 7/1996 | Yoon |
| 5,556,388 A | 9/1996 | Johlin, Jr. |
| 5,558,641 A | 9/1996 | Glantz et al. |
| 5,562,617 A | 10/1996 | Finch, Jr. et al. |
| 5,571,104 A | 11/1996 | Li |
| 5,575,777 A | 11/1996 | Cover et al. |
| 5,601,604 A | 2/1997 | Vincent |
| 5,637,102 A | 6/1997 | Tolkoff et al. |
| 5,653,755 A | 8/1997 | Ledergerber |
| 5,658,298 A | 8/1997 | Vincent et al. |
| 5,674,397 A | 10/1997 | Pawlak et al. |
| 5,683,447 A | 11/1997 | Bush et al. |
| 5,688,237 A | 11/1997 | Rozga et al. |
| 5,695,490 A | 12/1997 | Flaherty et al. |
| 5,716,342 A | 2/1998 | Dumbraveanu et al. |
| 5,718,682 A | 2/1998 | Tucker |
| 5,722,957 A | 3/1998 | Steinbach |
| 5,748,200 A | 5/1998 | Funahashi |
| 5,810,735 A | 9/1998 | Halperin et al. |
| 5,814,019 A | 9/1998 | Steinbach et al. |
| 5,833,654 A | 11/1998 | Powers et al. |
| 5,843,033 A | 12/1998 | Ropiak |
| RE36,176 E | 3/1999 | Kuzmak |
| 5,883,654 A | 3/1999 | Katsuyama |
| 5,902,598 A | 5/1999 | Chen et al. |
| 5,906,596 A | 5/1999 | Tallarida |
| 5,910,149 A | 6/1999 | Kuzmak |
| 5,911,704 A | 6/1999 | Humes |
| 5,931,829 A | 8/1999 | Burbank et al. |
| 5,932,460 A | 8/1999 | Mills et al. |
| 5,935,083 A | 8/1999 | Williams |
| 5,938,669 A | 8/1999 | Klaiber et al. |
| 5,951,512 A | 9/1999 | Dalton |
| 6,024,704 A | 2/2000 | Meador et al. |
| 6,030,369 A | 2/2000 | Engelson et al. |
| 6,039,712 A | 3/2000 | Fogarty et al. |
| 6,074,341 A | 6/2000 | Anderson et al. |
| 6,090,066 A | 7/2000 | Schnell |
| 6,098,405 A | 8/2000 | Miyata et al. |
| 6,102,678 A | 8/2000 | Peclat |
| 6,102,922 A | 8/2000 | Jakobsson et al. |
| 6,123,700 A | 9/2000 | Mills et al. |
| 6,152,885 A | 11/2000 | Taepke |
| 6,171,252 B1 | 1/2001 | Roberts |
| 6,183,449 B1 | 2/2001 | Sibbitt |
| 6,213,973 B1 | 4/2001 | Eliasen et al. |
| 6,221,024 B1 | 4/2001 | Miesel |
| 6,234,973 B1 | 5/2001 | Meador et al. |
| 6,258,079 B1 | 7/2001 | Burbank et al. |
| 6,264,676 B1 | 7/2001 | Gellman et al. |
| 6,283,949 B1 | 9/2001 | Roorda |
| 6,321,124 B1 | 11/2001 | Cigaina |
| 6,349,740 B1 | 2/2002 | Cho et al. |
| 6,432,040 B1 | 8/2002 | Meah |
| 6,450,946 B1 | 9/2002 | Forsell |
| 6,453,907 B1 | 9/2002 | Forsell |
| 6,454,699 B1 | 9/2002 | Forsell |
| 6,459,917 B1 | 10/2002 | Gowda et al. |
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent et al. |
| 6,572,587 B2 | 6/2003 | Lerman et al. |
| 6,589,184 B2 | 7/2003 | Noren et al. |
| 6,648,849 B2 | 11/2003 | Tenhuisen et al. |
| 6,666,845 B2 | 12/2003 | Hooper et al. |
| 6,689,100 B2 | 2/2004 | Connelly et al. |
| 6,723,053 B2 | 4/2004 | Ackerman et al. |
| 6,733,519 B2 | 5/2004 | Lashinski et al. |
| 6,792,309 B1 | 9/2004 | Noren |
| 6,810,880 B1 | 11/2004 | Jennings, Jr. et al. |
| 6,813,964 B1 | 11/2004 | Clark et al. |
| 6,860,857 B2 | 3/2005 | Noren et al. |
| 6,915,162 B2 | 7/2005 | Noren et al. |
| 6,921,267 B2 | 7/2005 | van Oostrom et al. |
| 6,929,631 B1 | 8/2005 | Brugger et al. |

| | | | |
|---|---|---|---|
| 6,939,299 B1 | 9/2005 | Petersen et al. | |
| 6,953,444 B2 | 10/2005 | Rosenberg | |
| 6,964,204 B2 | 11/2005 | Clark et al. | |
| 6,966,875 B1 | 11/2005 | Longobardi | |
| 6,997,914 B2 | 2/2006 | Smith et al. | |
| 7,017,583 B2 | 3/2006 | Forsell | |
| 7,020,531 B1 | 3/2006 | Colliou et al. | |
| 7,056,286 B2 | 6/2006 | Ravenscroft et al. | |
| 7,063,669 B2 | 6/2006 | Brawner et al. | |
| 7,073,387 B2 | 7/2006 | Zdeblick et al. | |
| 7,082,843 B2 | 8/2006 | Clark et al. | |
| 7,131,945 B2 | 11/2006 | Fink et al. | |
| 7,144,400 B2 | 12/2006 | Byrum et al. | |
| 7,149,587 B2 | 12/2006 | Wardle et al. | |
| 7,191,007 B2 | 3/2007 | Desai et al. | |
| 7,195,774 B2 | 3/2007 | Carvalho et al. | |
| 7,223,239 B2 | 5/2007 | Schulze | |
| 7,226,419 B2 | 6/2007 | Lane et al. | |
| 7,261,003 B2 | 8/2007 | McDonald et al. | |
| 7,267,645 B2 | 9/2007 | Anderson et al. | |
| 7,282,023 B2 | 10/2007 | Frering | |
| 7,311,716 B2 | 12/2007 | Byrum | |
| 7,311,717 B2 | 12/2007 | Egle | |
| 7,351,198 B2 | 4/2008 | Byrum et al. | |
| 7,351,226 B1 | 4/2008 | Herskowitz | |
| 7,351,240 B2 | 4/2008 | Hassler, Jr. et al. | |
| 7,353,747 B2 | 4/2008 | Swayze et al. | |
| 7,364,542 B2 | 4/2008 | Jambor et al. | |
| 7,367,937 B2 | 5/2008 | Jambor et al. | |
| 7,374,557 B2 | 5/2008 | Conlon | |
| 7,374,565 B2 | 5/2008 | Hassler, Jr. et al. | |
| 7,390,294 B2 | 6/2008 | Hassler, Jr. | |
| 7,413,547 B1 | 8/2008 | Lichtscheidl et al. | |
| 7,416,528 B2 | 8/2008 | Crawford et al. | |
| 7,437,951 B2 | 10/2008 | McDonald et al. | |
| 7,438,718 B2 | 10/2008 | Milliman et al. | |
| 7,445,614 B2 | 11/2008 | Bunodiere et al. | |
| 7,468,038 B2 | 12/2008 | Ye et al. | |
| 7,500,944 B2 | 3/2009 | Byrum et al. | |
| 7,510,530 B2 | 3/2009 | Hashimoto et al. | |
| 7,530,943 B2 | 5/2009 | Lechner | |
| 7,553,298 B2 | 6/2009 | Hunt | |
| 7,561,916 B2 | 7/2009 | Hunt | |
| 7,580,746 B2 | 8/2009 | Gilkerson et al. | |
| 7,591,185 B1 | 9/2009 | Mothilal et al. | |
| 7,593,777 B2 | 9/2009 | Gerber | |
| 7,634,319 B2 | 12/2009 | Schneider et al. | |
| 7,651,483 B2 | 1/2010 | Byrum | |
| 7,658,196 B2 | 2/2010 | Ferreri et al. | |
| 7,699,770 B2 | 4/2010 | Hassler, Jr. et al. | |
| 7,708,722 B2 | 5/2010 | Glenn | |
| 7,762,998 B2 | 7/2010 | Birk et al. | |
| 7,762,999 B2 | 7/2010 | Byrum | |
| 7,775,215 B2 | 8/2010 | Hassler, Jr. et al. | |
| 7,775,966 B2 | 8/2010 | Dlugos et al. | |
| 7,811,275 B2 | 10/2010 | Birk et al. | |
| 7,850,660 B2 | 12/2010 | Uth et al. | |
| 7,862,546 B2 | 1/2011 | Conlon et al. | |
| 7,909,754 B2 | 3/2011 | Hassler, Jr. et al. | |
| 7,909,804 B2 | 3/2011 | Stats | |
| 8,007,474 B2 | 8/2011 | Uth et al. | |
| 2002/0013545 A1 | 1/2002 | Soltanpour et al. | |
| 2002/0058969 A1 | 5/2002 | Noren et al. | |
| 2002/0087147 A1 | 7/2002 | Hooper et al. | |
| 2002/0095181 A1 | 7/2002 | Beyar | |
| 2002/0139208 A1 | 10/2002 | Yatskov | |
| 2002/0198548 A1 | 12/2002 | Robert | |
| 2003/0045800 A1 | 3/2003 | Noren et al. | |
| 2003/0045910 A1 | 3/2003 | Sorensen et al. | |
| 2003/0073880 A1 | 4/2003 | Polsky et al. | |
| 2003/0078506 A1 | 4/2003 | Noren et al. | |
| 2003/0139690 A1 | 7/2003 | Aebli et al. | |
| 2004/0064110 A1 | 4/2004 | Forsell | |
| 2004/0065615 A1 | 4/2004 | Hooper et al. | |
| 2004/0068233 A1* | 4/2004 | DiMatteo | 604/177 |
| 2004/0082908 A1 | 4/2004 | Whitehurst et al. | |
| 2004/0111050 A1 | 6/2004 | Smedley et al. | |
| 2004/0204692 A1 | 10/2004 | Eliasen | |
| 2004/0254536 A1 | 12/2004 | Conlon et al. | |
| 2004/0254537 A1 | 12/2004 | Conlon | |
| 2004/0260229 A1 | 12/2004 | Meir | |
| 2004/0260319 A1 | 12/2004 | Egle | |
| 2004/0267288 A1 | 12/2004 | Byrum et al. | |
| 2004/0267291 A1 | 12/2004 | Byrum et al. | |
| 2004/0267292 A1 | 12/2004 | Byrum et al. | |
| 2004/0267293 A1 | 12/2004 | Byrum et al. | |
| 2004/0267377 A1 | 12/2004 | Egle | |
| 2005/0010177 A1 | 1/2005 | Tsai | |
| 2005/0049578 A1 | 3/2005 | Tu et al. | |
| 2005/0070875 A1 | 3/2005 | Kulessa | |
| 2005/0070937 A1 | 3/2005 | Jambor et al. | |
| 2005/0085778 A1 | 4/2005 | Parks | |
| 2005/0092093 A1 | 5/2005 | Kang et al. | |
| 2005/0131325 A1 | 6/2005 | Chen et al. | |
| 2005/0131352 A1 | 6/2005 | Conlon | |
| 2005/0131383 A1 | 6/2005 | Chen et al. | |
| 2005/0148956 A1 | 7/2005 | Conlon | |
| 2005/0149143 A1 | 7/2005 | Libbus et al. | |
| 2005/0209573 A1 | 9/2005 | Brugger et al. | |
| 2005/0240155 A1 | 10/2005 | Conlon | |
| 2005/0240156 A1 | 10/2005 | Conlon | |
| 2005/0267500 A1 | 12/2005 | Hassler, Jr. et al. | |
| 2005/0277899 A1 | 12/2005 | Conlon | |
| 2005/0283041 A1 | 12/2005 | Egle | |
| 2005/0283118 A1* | 12/2005 | Uth et al. | 604/175 |
| 2005/0283119 A1 | 12/2005 | Uth | |
| 2006/0074439 A1 | 4/2006 | Garner et al. | |
| 2006/0122578 A1 | 6/2006 | Lord et al. | |
| 2006/0161186 A1 | 7/2006 | Hassler, Jr. et al. | |
| 2006/0173423 A1 | 8/2006 | Conlon | |
| 2006/0173424 A1 | 8/2006 | Conlon | |
| 2006/0178647 A1 | 8/2006 | Stats | |
| 2006/0178648 A1 | 8/2006 | Barron et al. | |
| 2006/0184141 A1 | 8/2006 | Smith et al. | |
| 2006/0189887 A1 | 8/2006 | Hassler, Jr. et al. | |
| 2006/0189888 A1 | 8/2006 | Hassler, Jr. et al. | |
| 2006/0190039 A1* | 8/2006 | Birk et al. | 606/219 |
| 2006/0199997 A1 | 9/2006 | Hassler, Jr. et al. | |
| 2006/0211912 A1 | 9/2006 | Dlugos et al. | |
| 2006/0211913 A1 | 9/2006 | Dlugos et al. | |
| 2006/0211914 A1 | 9/2006 | Hassler, Jr. et al. | |
| 2006/0217668 A1 | 9/2006 | Schulze et al. | |
| 2006/0217673 A1 | 9/2006 | Schulze | |
| 2006/0235445 A1* | 10/2006 | Birk et al. | 606/151 |
| 2006/0235448 A1 | 10/2006 | Roslin et al. | |
| 2006/0247539 A1 | 11/2006 | Schugt et al. | |
| 2006/0266128 A1 | 11/2006 | Clark et al. | |
| 2006/0293625 A1 | 12/2006 | Hunt et al. | |
| 2006/0293626 A1 | 12/2006 | Byrum et al. | |
| 2006/0293627 A1 | 12/2006 | Byrum | |
| 2006/0293628 A1 | 12/2006 | Hunt et al. | |
| 2007/0010790 A1 | 1/2007 | Byrum et al. | |
| 2007/0015954 A1 | 1/2007 | Dlugos | |
| 2007/0015955 A1 | 1/2007 | Tsonton | |
| 2007/0016231 A1 | 1/2007 | Jambor et al. | |
| 2007/0027356 A1 | 2/2007 | Ortiz | |
| 2007/0038255 A1 | 2/2007 | Kieval et al. | |
| 2007/0060959 A1 | 3/2007 | Salo et al. | |
| 2007/0073250 A1 | 3/2007 | Schneiter | |
| 2007/0078391 A1 | 4/2007 | Wortley | |
| 2007/0088336 A1 | 4/2007 | Dalton | |
| 2007/0088391 A1 | 4/2007 | McAlexander | |
| 2007/0129765 A1 | 6/2007 | Gilkerson et al. | |
| 2007/0135758 A1 | 6/2007 | Childers et al. | |
| 2007/0149947 A1 | 6/2007 | Byrum | |
| 2007/0156013 A1 | 7/2007 | Birk | |
| 2007/0158769 A1 | 7/2007 | You | |
| 2007/0161958 A1 | 7/2007 | Glenn | |
| 2007/0167672 A1 | 7/2007 | Dlugos et al. | |
| 2007/0173685 A1 | 7/2007 | Jambor et al. | |
| 2007/0185462 A1 | 8/2007 | Byrum | |
| 2007/0191717 A1 | 8/2007 | Rosen et al. | |
| 2007/0205384 A1 | 9/2007 | Kurosawa | |
| 2007/0208313 A1 | 9/2007 | Conlon | |
| 2007/0213837 A1 | 9/2007 | Ferreri et al. | |
| 2007/0219510 A1 | 9/2007 | Zinn et al. | |
| 2007/0235083 A1 | 10/2007 | Dlugos | |
| 2007/0250086 A1 | 10/2007 | Wiley et al. | |

| | | | | | | |
|---|---|---|---|---|---|---|
| 2007/0255165 | A1 | 11/2007 | Uesugi et al. | 2010/0191271 A1 | 7/2010 | Lau et al. |
| 2007/0255234 | A1 | 11/2007 | Haase et al. | 2010/0211085 A1 | 8/2010 | Uth et al. |
| 2007/0265666 | A1 | 11/2007 | Roberts et al. | 2010/0217198 A1 | 8/2010 | Franklin et al. |
| 2007/0282196 | A1 | 12/2007 | Birk et al. | 2010/0217199 A1 | 8/2010 | Uth et al. |
| 2007/0293829 | A1 | 12/2007 | Conlon et al. | 2010/0217200 A1 | 8/2010 | Uth et al. |
| 2008/0009680 | A1 | 1/2008 | Hassler, Jr. | 2010/0228080 A1 | 9/2010 | Tavori et al. |
| 2008/0015406 | A1 | 1/2008 | Dlugos et al. | 2010/0234808 A1 | 9/2010 | Uth et al. |
| 2008/0039772 | A1 | 2/2008 | Chantriaux et al. | 2011/0054407 A1 * | 3/2011 | Olroyd et al. .................. 604/174 |
| 2008/0058632 | A1 | 3/2008 | Tai et al. | 2011/0082426 A1 | 4/2011 | Conlon et al. |
| 2008/0097496 | A1 | 4/2008 | Chang et al. | 2011/0251453 A1 * | 10/2011 | Honaryar et al. .................. 600/37 |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| JP | 2119877 | 5/1990 |
| JP | 8107934 | 4/1996 |
| SU | 1823791 | 6/1991 |
| WO | WO 94/22520 | 10/1994 |
| WO | WO 96/40357 | 12/1996 |
| WO | WO 97/01370 | 1/1997 |
| WO | WO 99/20338 | 4/1999 |
| WO | WO 99/26543 | 6/1999 |
| WO | WO 99/34859 | 7/1999 |
| WO | WO 00/15158 | 3/2000 |
| WO | WO 00/33901 | 6/2000 |
| WO | WO 01/10359 | 2/2001 |
| WO | WO 01/49245 | 7/2001 |
| WO | WO 01/80926 | 11/2001 |
| WO | WO 01/95813 | 12/2001 |
| WO | WO 02/074381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

| | | | |
|---|---|---|---|
| 2008/0114308 | A1 | 5/2008 | di Palma et al. |
| 2008/0119798 | A1 | 5/2008 | Chantriaux et al. |
| 2008/0243093 | A1 | 10/2008 | Kalpin et al. |
| 2008/0249806 | A1 | 10/2008 | Dlugos et al. |
| 2008/0250340 | A1 | 10/2008 | Dlugos et al. |
| 2008/0250341 | A1 | 10/2008 | Dlugos et al. |
| 2008/0255403 | A1 | 10/2008 | Voegele et al. |
| 2008/0255414 | A1 | 10/2008 | Voegele et al. |
| 2008/0255425 | A1 | 10/2008 | Voegele et al. |
| 2008/0255459 | A1 | 10/2008 | Voegele et al. |
| 2008/0255537 | A1 | 10/2008 | Voegele et al. |
| 2008/0281412 | A1 | 11/2008 | Smith et al. |
| 2008/0287969 | A1 | 11/2008 | Tsonton et al. |
| 2008/0287974 | A1 | 11/2008 | Widenhouse et al. |
| 2008/0312553 | A1 | 12/2008 | Timmons |
| 2008/0319435 | A1 | 12/2008 | Rioux et al. |
| 2009/0018608 | A1 | 1/2009 | Schwartz et al. |
| 2009/0048524 | A1 | 2/2009 | Wildau et al. |
| 2009/0054914 | A1 | 2/2009 | Lechner |
| 2009/0062825 | A1 | 3/2009 | Pool et al. |
| 2009/0071258 | A1 | 3/2009 | Kouda et al. |
| 2009/0076466 | A1 | 3/2009 | Quebbemann et al. |
| 2009/0082757 | A1 | 3/2009 | Rogers et al. |
| 2009/0082793 | A1 | 3/2009 | Birk |
| 2009/0093768 | A1 | 4/2009 | Conlon et al. |
| 2009/0099538 | A1 | 4/2009 | Paganon |
| 2009/0105735 | A1 | 4/2009 | Stam et al. |
| 2009/0112308 | A1 | 4/2009 | Kassem |
| 2009/0118572 | A1 | 5/2009 | Lechner |
| 2009/0149874 | A1 | 6/2009 | Ortiz et al. |
| 2009/0157106 | A1 | 6/2009 | Marcotte |
| 2009/0157107 | A1 | 6/2009 | Kierath et al. |
| 2009/0157113 | A1 | 6/2009 | Marcotte et al. |
| 2009/0171375 | A1 | 7/2009 | Coe et al. |
| 2009/0171378 | A1 | 7/2009 | Coe et al. |
| 2009/0171379 | A1 | 7/2009 | Coe et al. |
| 2009/0192404 | A1 | 7/2009 | Ortiz et al. |
| 2009/0192415 | A1 | 7/2009 | Ortiz et al. |
| 2009/0192533 | A1 | 7/2009 | Dlugos, Jr. et al. |
| 2009/0192534 | A1 | 7/2009 | Ortiz et al. |
| 2009/0192541 | A1 | 7/2009 | Ortiz et al. |
| 2009/0198261 | A1 | 8/2009 | Schweikert |
| 2009/0202387 | A1 | 8/2009 | Dlugos, Jr. et al. |
| 2009/0204131 | A1 | 8/2009 | Ortiz et al. |
| 2009/0204132 | A1 | 8/2009 | Ortiz et al. |
| 2009/0209995 | A1 | 8/2009 | Byrum et al. |
| 2009/0216255 | A1 | 8/2009 | Coe et al. |
| 2009/0221974 | A1 | 9/2009 | Paganon |
| 2009/0222031 | A1 | 9/2009 | Axelsson |
| 2009/0222065 | A1 | 9/2009 | Dlugos, Jr. et al. |
| 2009/0227862 | A1 | 9/2009 | Smith et al. |
| 2009/0228028 | A1 | 9/2009 | Coe |
| 2009/0228072 | A1 | 9/2009 | Coe et al. |
| 2009/0248125 | A1 | 10/2009 | Brostrom |
| 2009/0248126 | A1 | 10/2009 | Nippoldt et al. |
| 2009/0254052 | A1 | 10/2009 | Birk et al. |
| 2009/0259190 | A1 | 10/2009 | Birk et al. |
| 2009/0259191 | A1 | 10/2009 | Birk et al. |
| 2009/0259231 | A1 | 10/2009 | Birk et al. |
| 2009/0264901 | A1 | 10/2009 | Franklin |
| 2009/0299216 | A1 | 12/2009 | Chen et al. |
| 2009/0299672 | A1 | 12/2009 | Zhang et al. |
| 2009/0306462 | A1 | 12/2009 | Lechner |
| 2009/0308169 | A1 | 12/2009 | Mothilal et al. |
| 2010/0087843 | A1 | 4/2010 | Bertolote et al. |
| 2010/0100079 | A1 | 4/2010 | Berkcan et al. |
| 2010/0114149 | A1 | 5/2010 | Albrecht et al. |
| 2010/0130941 | A1 | 5/2010 | Conlon et al. |
| 2010/0152532 | A1 | 6/2010 | Marcotte |

OTHER PUBLICATIONS

Autumn K. et al.; "Evidence of Van Der Waals Adhesion in Gecko Setae"; PNAS; vol. 99; No. 19; pp. 12252-12256; Sep. 17, 2012.

Geim AK. et al.; "Microfabricated Adhesive Mimicking Gecko Foot-Hair"; Nature Materials Abstract only; vol. 2; No. 7; 2003.

Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.

Yurdumakan B., et al.; "Synthetic Gecko Foot-Hairs from Multiwalled Carbon Nanotubes"; The Royal Society of Chemistry; p. 3799-3801; 2005.

Helioscopie Product Insert for Heliogast, pp. 1-11 (undated).

* cited by examiner

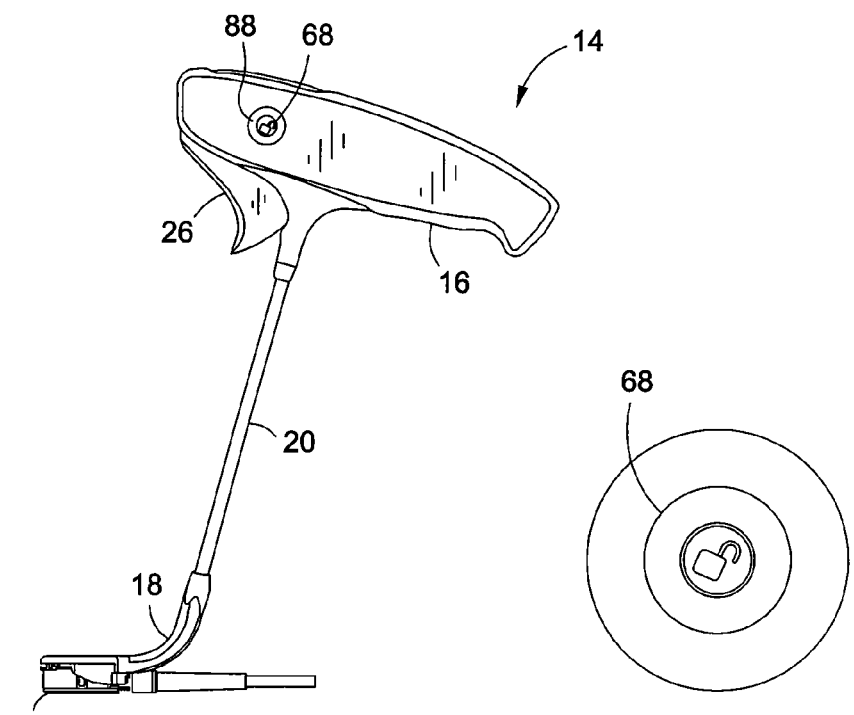
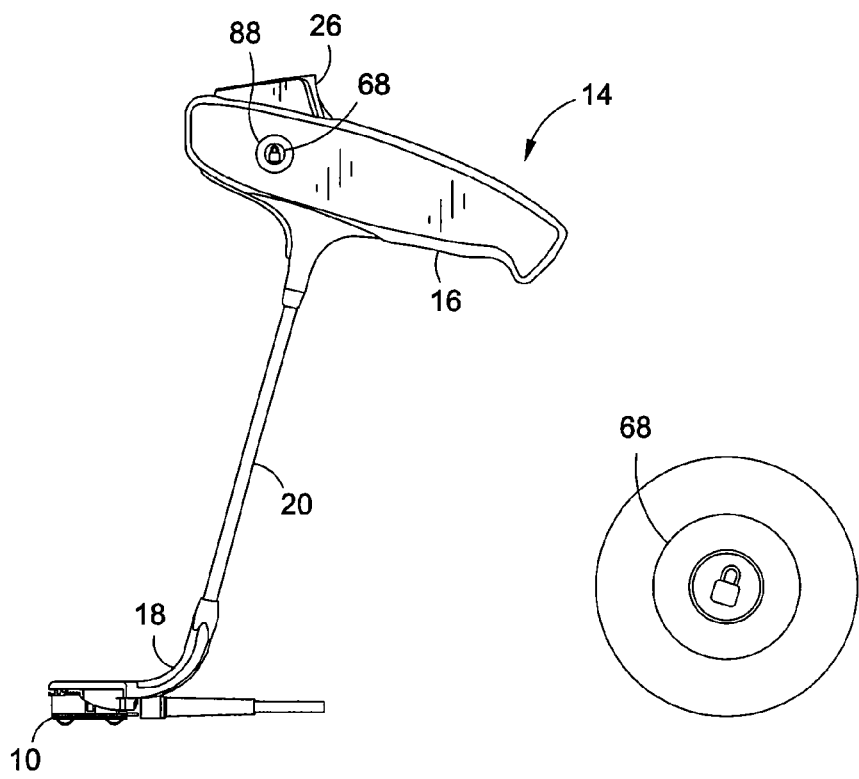

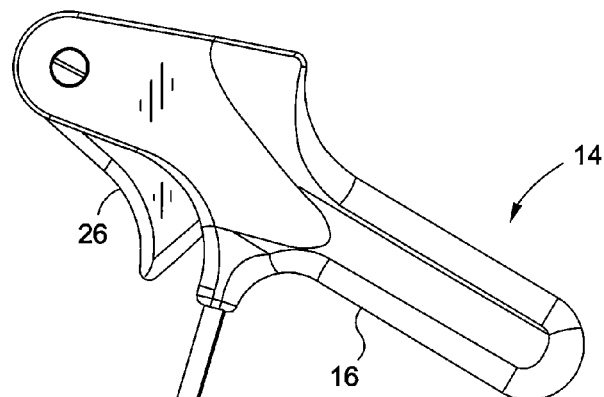
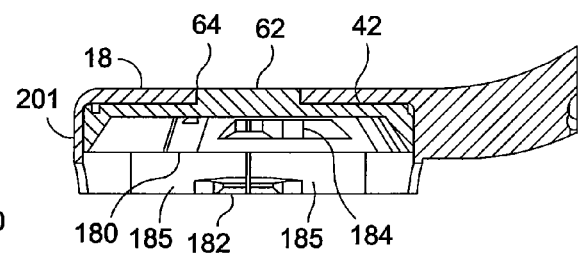
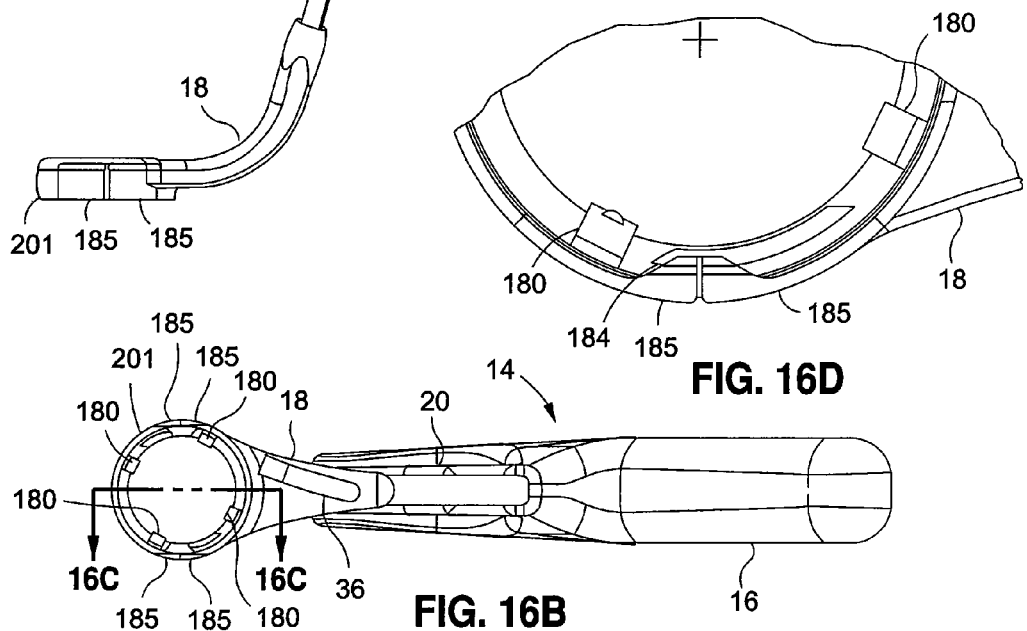
FIG. 16A
FIG. 16C
FIG. 16D
FIG. 16B

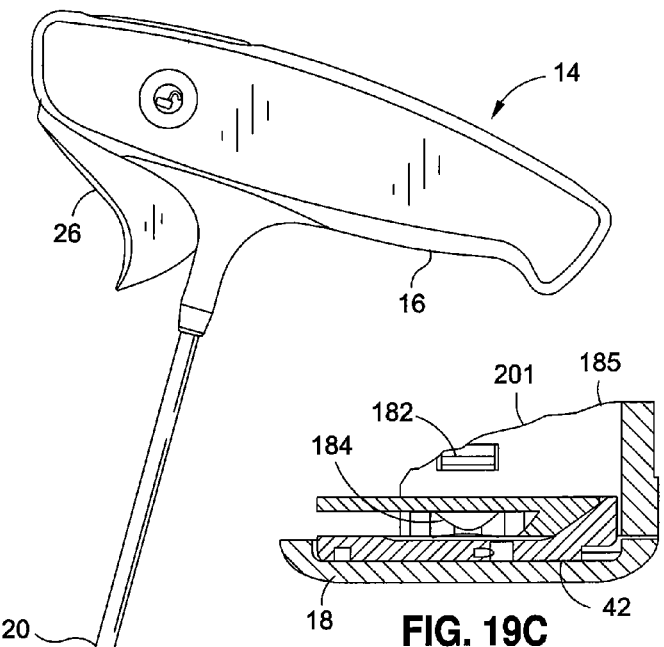
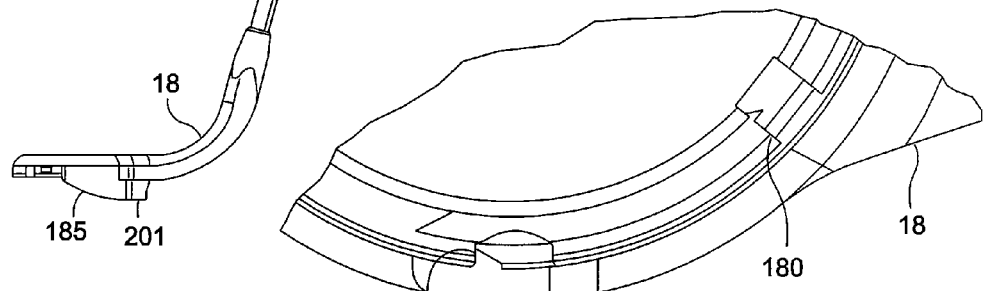
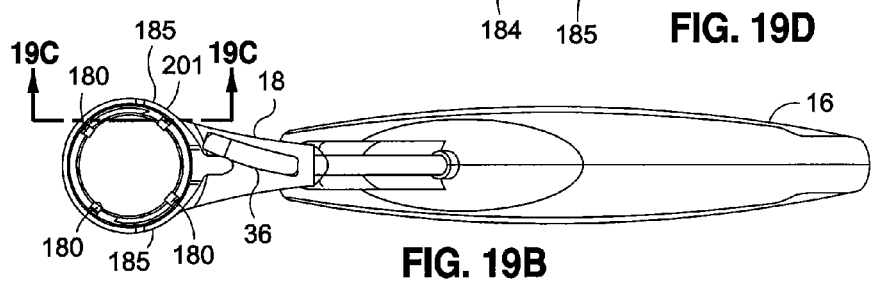
FIG. 19A
FIG. 19C
FIG. 19D
FIG. 19B

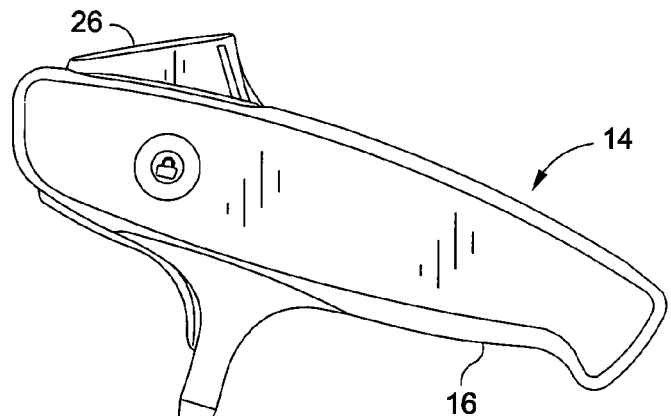
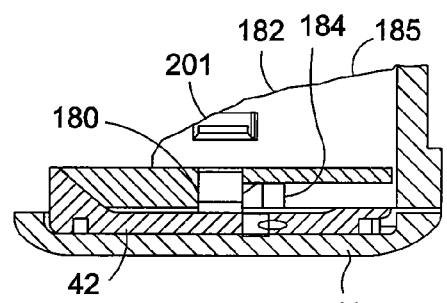
FIG. 20A
FIG. 20C
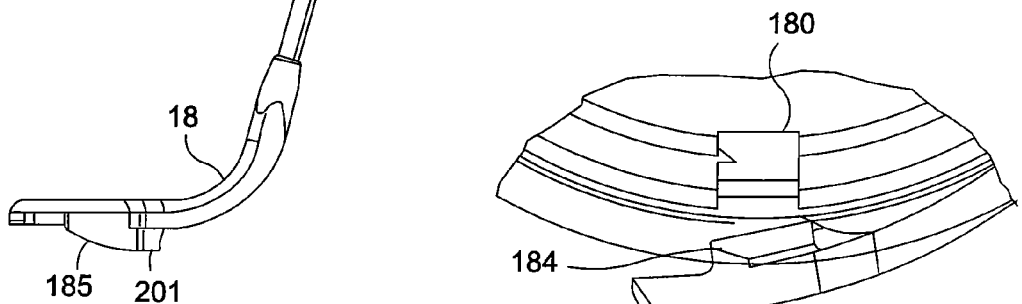
FIG. 20D
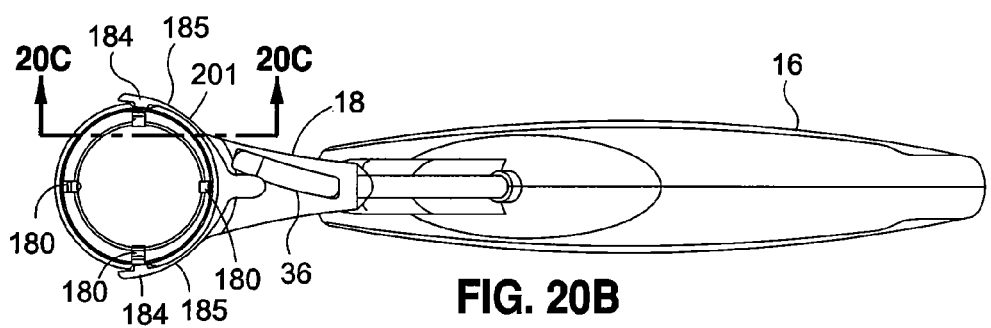
FIG. 20B

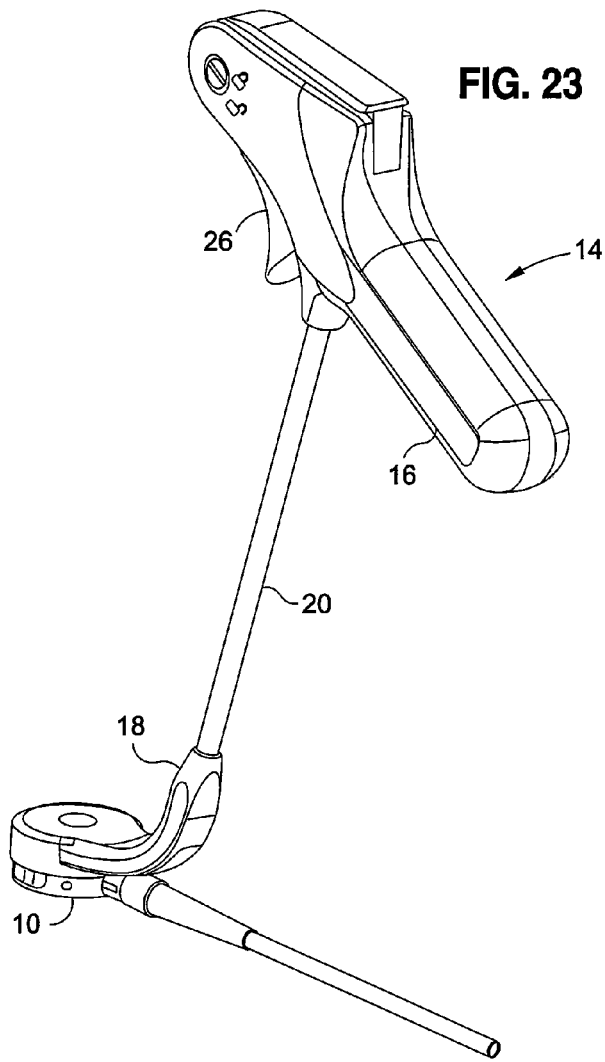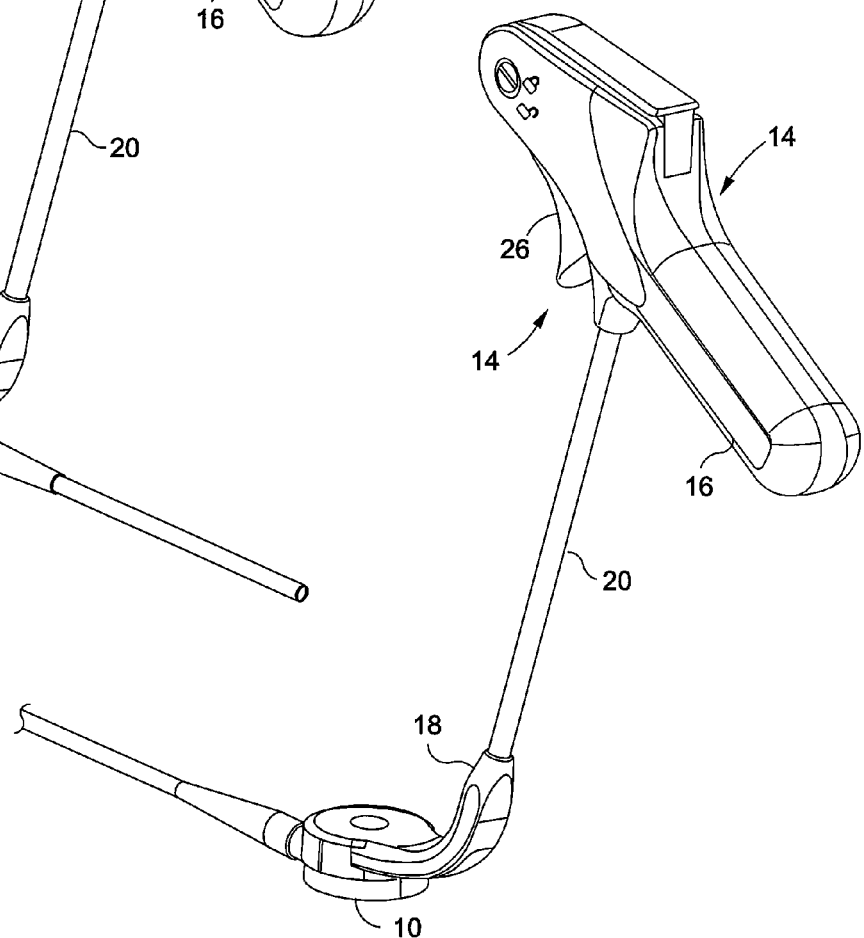

SYSTEM INCLUDING ACCESS PORT AND APPLICATOR TOOL

RELATED APPLICATIONS

The present Application for Patent claims priority to and the benefit of U.S. Provisional Patent Application Ser. No. 61/236,869, filed on Aug. 26, 2009, and U.S. Provisional Patent Application Ser. No. 61/237,641, filed on Aug. 27, 2009, both Applications hereby expressly incorporated by reference herein.

FIELD

The present invention generally relates to medical systems and apparatus and uses thereof for treating obesity and/or obesity-related diseases, and more specifically, relates to access ports and tools for applying same to bodily tissue.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts food's passage into a lower portion of the stomach. When the stoma is of an appropriate size that is restricted by a gastric band, food held in the upper portion of the stomach provides a feeling of satiety or fullness that discourages overeating. Unlike gastric bypass procedures, gastric band apparatus are reversible and require no permanent modification to the gastrointestinal tract.

Medical implants, including gastric band systems, for performing therapeutic functions for a patient are well known. Such devices include pace makers, vascular access ports, injection ports (such as used with gastric banding systems) and gastric pacing devices. Such implants need to be attached, typically subcutaneously, in an appropriate place in order to function properly. It is desirable that the procedure to implant such devices be quick, easy and efficient and require as small of an incision as possible.

SUMMARY

The present invention, in one aspect, provides a system for attaching a fluid access port to a patient. The system generally comprises an implantable access port and a tool for attaching an access port to a patient. The access port may be latched onto an interior portion, or muscle portion of a patient through various methods described herein.

In another aspect of the invention, access ports, or access port assemblies are provided. An access port assembly in accordance with the invention can be used in place of a conventional access port assembly designed to be used for facilitating inflation and deflation of a gastric band.

In yet another aspect of the invention, tools for securing a fluid access port assembly to a patient are provided.

In one embodiment, an access port assembly(is provided which comprises a septum, for example, a self-sealing septum, for receiving a needle, and a plurality of anchor assemblies, spaced apart from the septum. Each of the anchor assemblies is rotatable from a deployed position to an undeployed position. In one embodiment, each of the anchor assemblies is rotatable between a retracted or undeployed position, a midway position and a deployed position.

In one embodiment, each anchor assembly is a composite element. For example, each anchor assembly may be made of at least two different materials. In an exemplary embodiment, the anchor assembly includes a wire portion, for example made of a suitable metal, and a molded portion, for example, made of a polymer material, such as a suitable plastic, fixed to the wire portion.

In one embodiment, each anchor assembly is made of a bioresorbable material. A portion of each anchor assembly, or the entirety of each anchor assembly may be made of one or more bioresorbable materials.

The wire portion may include a curved region and a distal tip structured to penetrate and engage tissue. The molded portion is fixed to the wire portion, or molded to the wire portion. In one embodiment, the molded portion comprises a material which is overmolded to the wire portion. The molded portion may be molded or overmolded to a proximal region of the wire portion.

The molded portion may include a pivot axle substantially perpendicular to the plane of rotation of the wire portion. The molded portion may further comprise an actuator pin and a deploy pin spaced apart from the actuator pin.

In one embodiment, the rotation of an outer housing, or actuator, of the port causes each anchor assembly to rotate from the undeployed position to the deployed position. This may be accomplished by simply rotating the outer housing by hand which causes the anchor assemblies to deploy. Once deployed, there may be an audible "snap" to alert the physician that the anchors are fully deployed.

The anchor assembly and the actuator may be structured such that a torque applied to the anchor assembly increases as the anchor assemblies move from a retracted position to a deployed position.

In another aspect of the invention, an access port assembly is provided which comprises a septum, a housing secured to the septum and include a base substantially opposing the septum. The access port further comprises a plurality of anchors, for example, the anchor assemblies described elsewhere herein. In this particular embodiment, the access port assembly further comprises an attachment member, for example, a mesh member, secured to the base for encouraging tissue ingrowth when the port assembly is implanted in a patient. The mesh member is disposed along at least a portion of the housing and is effective to encourage or promote tissue ingrowth or tissue engagement after the access port assembly has been implanted in the patient.

In one embodiment, the mesh member does not substantially extend beyond the base. In another embodiment, the mesh member includes a portion extending beyond the base. For example, the portion of the mesh may extend outwardly from and substantially circumscribe the base.

Attachment of the mesh material may be accomplished in any suitable manner. For example, a size of mesh can be manually attached to a mesh ring that snaps to the bottom of the port (e.g., the base of the port). Alternatively, the mesh member can be ultrasonically welded to the bottom of a mesh ring that snaps onto the bottom of the port. In addition, the mesh member may be positioned between the mesh ring and the base of the port. Furthermore, the mesh member may be molded or overmolded to the base of the access port to form an integral member with the base. The mesh member may have an oversized shape that allows the mesh to be supplied with the port and cut to the desired size.

In another aspect of the invention, a coating of bioresorbable material may be placed over a portion or the entirety of the base.

In another aspect of the invention, the base of the access port itself may be made of one or more bioresorbable materials.

In another aspect of the invention, a pulpation ring, or locking ring, may be fixed to the access port housing to form a ring-shaped gap. In addition, a compression ring may be placed within the access port housing. A portion of the septum may enter into the ring-shaped gap and be compressed by the pulpation ring and the compression ring, to provide a blocking point to prevent fluid from exiting the access port. The ring-shaped gap may be sized such that a standard syringe needle can not penetrate the septum in the cavity.

In another aspect of the invention, a tool is provided for facilitating attachment of a port, for example, the access port assembly described and shown elsewhere herein, to bodily tissue. In one embodiment, the tool includes a handle having a trigger, and an actuator head structured to removably engage the port housing.

In a particularly advantageous embodiment, the actuator head is rotatable or pivotal with respect to the handle, which facilitates manipulation and positioning of the access port. In one embodiment, the actuator head is rotatable at least 90 degrees and in other embodiments, the actuator head is rotatable up to 180 degrees, or even 360 degrees.

In another aspect of the invention, the actuator head is structured to engage the port assembly in more than one position, or orientation with respect to the actuator head.

These and other aspects of the invention may be more clearly understood and/or appreciated by referring to the accompanying drawings and detailed description.

BRIEF DESCRIPTION OF THE DRAWINGS

FIGS. 5B and 5D each illustrate a side view of the tool according to an embodiment of the present invention.

FIGS. 5C and 5E each illustrate a close-up view of a status indicator according to an embodiment of the present invention.

FIG. 16A illustrates a side view of the tool according to an embodiment of the present invention.

FIG. 16B illustrates a bottom view of the tool according to an embodiment of the present invention.

FIG. 16C illustrates a side, cross sectional view of the actuator head according to an embodiment of the present invention.

FIG. 16D illustrates a close-up bottom view of a portion of the actuator head according to an embodiment of the present invention.

FIG. 19A illustrates a side view of the tool according to an embodiment of the present invention.

FIG. 19B illustrates a bottom view of the tool according to an embodiment of the present invention.

FIG. 19C illustrates a side, cross sectional view of the actuator head according to an embodiment of the present invention.

FIG. 19D illustrates a close-up bottom view of a portion of the actuator head according to an embodiment of the present invention.

FIG. 20A illustrates a side view of the tool according to an embodiment of the present invention.

FIG. 20B illustrates a bottom view of the tool according to an embodiment of the present invention.

FIG. 20C illustrates a side, cross sectional view of the actuator head according to an embodiment of the present invention.

FIG. 20D illustrates a close-up bottom view of a portion of the actuator head according to an embodiment of the present invention.

FIGS. 23 and 24 each illustrate a perspective view of the system according to an embodiment of the present invention.

DETAILED DESCRIPTION

The present invention relates to implantable medical devices and surgical instruments and fasteners, and more specifically to access ports and tools for applying same to bodily tissue.

Figure 1:
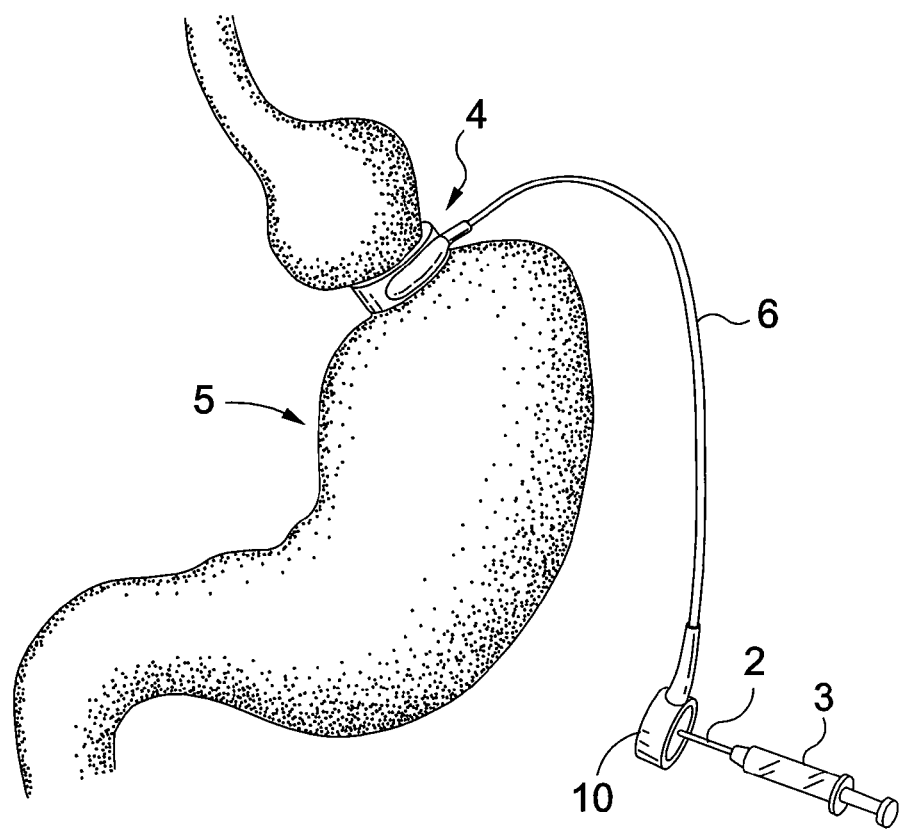
FIG. 1 illustrates a gastric band system according to an embodiment of the present invention.

As shown in FIG. 1, a simplified perspective view of an access port 10 of a system of the invention is shown. The access port 10 is shown as it is being penetrated by a needle 2 of a manually operable syringe 3. By passing fluid into the access port 10, or removing fluid by means of the access port 10, the needle 2 and syringe 3 provide a convenient means for inflating and/or deflating a conventional gastric band 4, thereby enabling adjustment of a size of a stoma or a level of restriction on a patient's stomach 5. The tube 6 passes the fluid from the access port 10 to and from the gastric band 4.

The access port 10 is generally fixed within the interior of a patient's body, preferably latched to a patient's abdominal muscle.

Figure 2A:
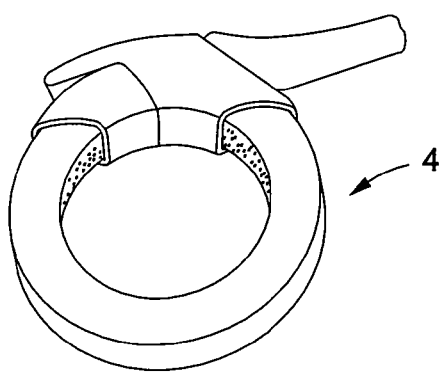
FIG. 2A illustrates a perspective view of the inner diameter of the band corresponding to a decreased volume of fluid in the gastric band according to an embodiment of the present invention.
Figure 2B:
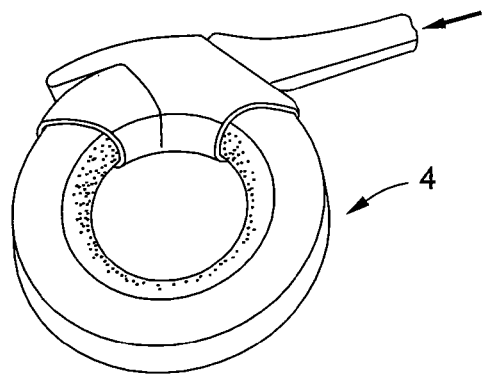
FIG. 2B illustrates a perspective view of the inner diameter of the band corresponding to an increased volume of fluid in the gastric band according to an embodiment of the present invention.

The gastric band 4 is shown in a deflated state in FIG. 2A and an inflated state in FIG. 2B, and is not considered, in itself, to make up an embodiment of the present invention.

Figures 3A, 3B:
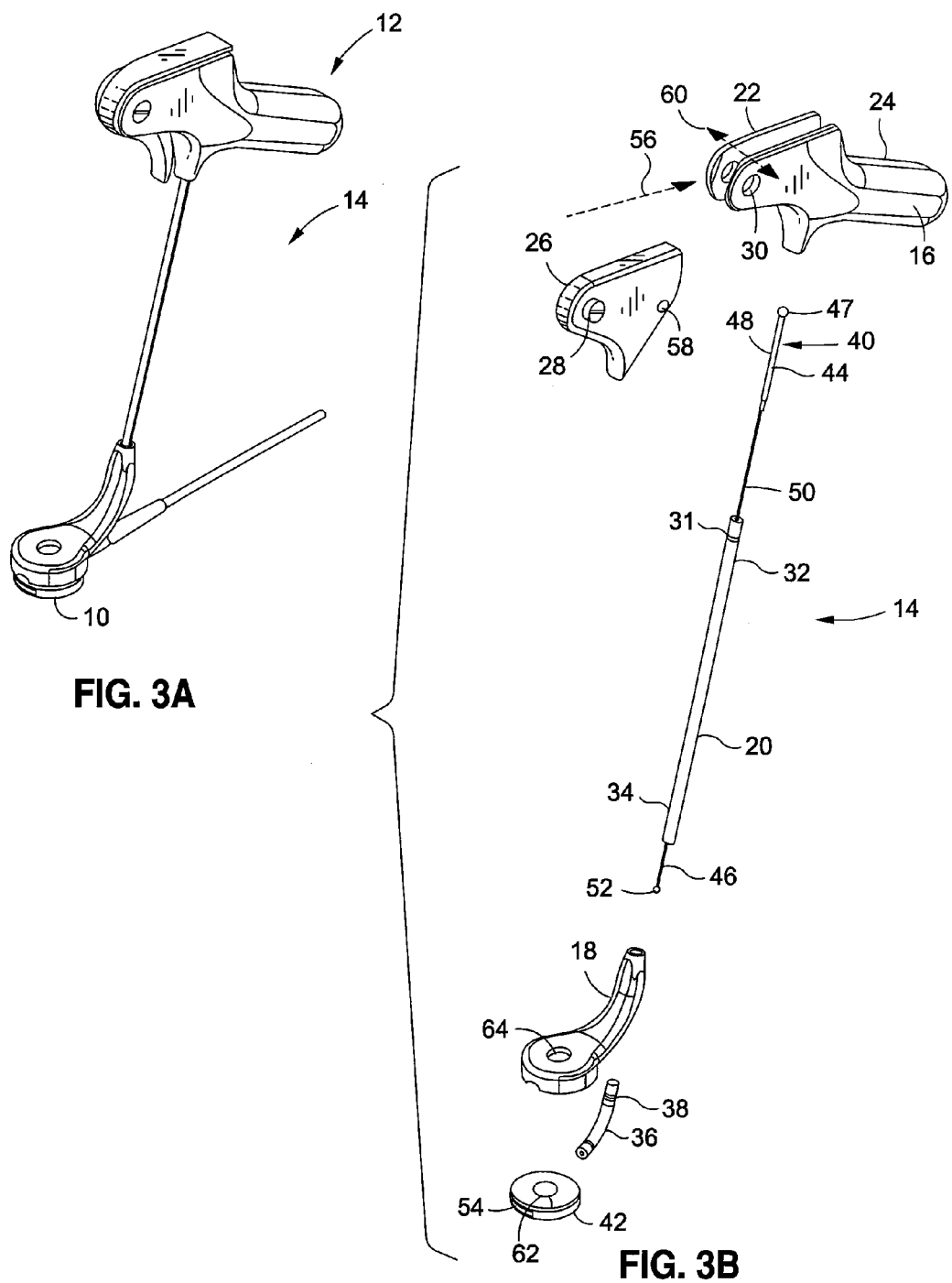
FIG. 3A illustrates a perspective view of the system of the present invention, including an access port and a tool according to an embodiment of the present invention.
FIG. 3B illustrates an exploded perspective view of the tool according to an embodiment of the present invention.

Turning now to FIG. 3A, a system 12 is provided for attaching the access port 10 to a portion of a patient's body. The system 12 generally comprises an implantable access port 10, and a tool 14 for attaching the access port 10 to the patient's body.

FIG. 3B illustrates an exploded view of the tool 14. In the shown embodiment, the tool 14 includes a handle 16 and an actuator head 18 coupled to the handle 16 through an extension tube 20. The handle 16 includes a trigger engagement portion 22 and a grip portion 24. The trigger engagement portion 22 may generally have a forked shape that retains and houses the manually operable trigger 26. The trigger 26 engages with the handle 16 through pins 28 located on the sides of the trigger 26 that pass through apertures 30 located along the sides of the trigger engagement portion 22. The trigger 26 is therefore retained, or bounded on two sides, in a slot formed by the forked ends of the trigger engagement portion 22. The grip portion 24 has a generally cylindrical shape, and is used by a user (e.g., a physician) to grip the tool 14 during operation.

The handle 16 couples to the actuator head 18 through a generally cylindrically shaped extension tube 20. The extension tube 20 has a hollow interior cavity that allows a cable assembly 40 to pass from the handle 16 to the actuator cap 42. A proximal portion 32 of the extension tube 20 may have a pivot device 31, or a slotted portion of the extension tube 20 that engages with the handle 16. The pivot device 31 may allow the extension tube 20 to pivot, swivel, or rotate with respect to the handle 16, and allow the actuator head 18 to pivot with respect to the handle 16, as shown in FIG. 4B. In addition, the pivot device 31 may not be used, but may rather be replaced with a threaded device, to securely engage the extension tube 20 with the handle 16, if the actuator head 18 is not configured to pivot. In one embodiment, both a threaded device and a pivot device, such as a swivel, may be used to couple the extension tube 20 to the handle 16. In this embodiment, the threaded device firmly fixes the extension tube 20 to the handle 16, yet the pivot device still allows the extension tube 20 to rotate with respect to the handle 16. Furthermore, in one embodiment, the pivot device 31 may be equivalently replaced with a swivel device, a sleeve device, or any equivalent mechanism that allows the extension tube 20 to rotate. In addition, the pivot device 31 may be configured to allow the extension tube 20 to pivot laterally in multiple dimensions around the handle 16, including a direction towards the handle 16, away from the handle 16, directions perpendicular to the handle 16, or combinations of these directions.

A distal end 34 of the extension tube 20 couples to the actuator head 18. In the embodiment shown in FIG. 3B, the extension tube 20 may couple to the extension tube 20 through a radius tube 36. The radius tube 36 has a generally cylindrical shape and a hollow interior cavity. The radius tube 36 is shaped to contour to a corresponding curved shape of the actuator head 18. A threaded portion 38 of the radius tube 36 at one end of the radius tube 36 may be threaded into an internally threaded portion of the extension tube 20. In addition, the radius tube 36 may also have a pivot device, similar to the pivot device 31 of the extension tube 20. In this embodiment, the pivot device of the radius tube 36 allows the radius head 36 to rotate with respect to the handle 16, or the extension tube 20. In this manner, the actuator head 18 may rotate with respect to the handle 16 in this embodiment. Similar to the pivot device 31 of the extension tube 20, the pivot device on the radius tube 36 may allow the actuator head 18 to rotate in multiple dimensions relative to the handle 16. The radius tube 36 may be housed within the interior of the actuator head 18, or may be positioned outside and below the actuator head 18. The orientation of the radius tube 36 may be more clearly viewed in FIGS. 16B, 17B, 19B, and 20B. The radius tube 36 serves to thread a portion of the cable assembly 40 from the handle 16 to the actuator cap 42.

The cable assembly 40 connects from the handle 16 to the actuator cap 42. The cable assembly 40 has a proximal portion 44 and a distal portion 46, with stiff, yet flexible, cable 50 extending between the portions 44, 46. The proximal portion 44 includes a ball 47, or a ball head, positioned at the end of the cable 50. The ball 47 engages the trigger 26. The proximal portion 44 may additionally include a sheath 48 that strengthens the proximal portion 44, and is positioned near the ball 47. The sheath 48 generally provides a resistance to damage to the cable 50 during operation of the tool 14. The sheath may be made of stainless steel, or the like. The sheath 48 may additionally constitute an attachment point from the cable 50 to the ball 47.

The cable 50 extends from the proximal portion 44 to the distal portion 46 of the cable assembly 40, and includes an attachment device 52 positioned at the distal portion 46. The attachment device 52 is configured to engage the actuator cap 42, and may include a ball device, a plug device, or the like. The cable 50 is preferably made from a stiff, yet flexible material, such as a threaded metal, nitinol, or the like. The cable 50 is made from a stiff material to allow the cable 50 to transmit both a pulling force and a pushing force to the actuator cap 42 when the tool 14 is operated.

During assembly of the tool 14, the radius tube 36 is installed into the actuator head 18 in the orientation shown in FIG. 3B. The threaded portion 38 of the radius tube 36 connects to an internally threaded portion of the extension tube 20. The connection between the radius tube 36 and the extension tube 20 locks the actuator head 18 in position, and also provides a tubular path for the cable assembly 40 to travel from the trigger 26 to the actuator cap 42. Because the extension tube 20 engages the radius tube 36, and not the actuator head 18 directly, the actuator head 18 is free to pivot with respect to the extension tube 20, if the radius tube 36 is pivotally connected to the extension tube 20.

The extension tube 20 is either threaded into the handle 16, to firmly secure the extension tube 20 in position with respect to the handle 16, or the pivot device 31 is engaged with a mating slot in the handle 26. The mating slot conforms to the shape of the pivot device 31, and will allow the extension tube 20 and actuator head 18 to rotate with respect to the handle 16. The actuator head 18 may rotate with respect to the handle 16 because the extension tube 20 is firmly fixed to the radius tube 36.

The actuator cable assembly 40 is then fed through the top of the handle 16 and into a Teflon tube that has a clearance fit inside the extension tube 20 and continues into the radius tube 36. The Teflon tube reduces friction and improves the tactile feedback to the trigger 26. The cable assembly 40 passes through the radius tube 36 and the distal end 46 of the cable assembly 40 is coupled to the actuator cap 42. More specifically, the attachment device 52 of the cable assembly 40 is fixed to the actuator cap 42 along a slotted groove 54 positioned along the top perimeter of the actuator cap 42. The slotted groove 54 may extend around a portion, or around the entire top surface of the actuator cap 42. The slotted groove 54 allows a slack portion of the cable 50 to wrap around the actuator cap 42 and further increases the total contact surface area between the cable 50 and the actuator cap 42. The increased contact surface area increases the torque strength transmitted from the cable 50 to the actuator cap 42.

The trigger 26 is inserted into the trigger engagement portion 22 in the direction shown by arrow 56. The pins 28 on the trigger 26 engage with the apertures 30, to allow the trigger 26 to rotate with respect to an axis of rotation 60.

When the trigger 26 is inserted into the trigger engagement portion 22, the ball 47 positioned at the proximal end 44 of the cable assembly 40 attaches to the trigger 26. A ball receiving structure 58 of the trigger 26 engages the ball 47 of the cable assembly 40. The ball receiving structure 58 may comprise a cavity to receive the ball 47, or any equivalent structure that retains the ball 47.

The connection between the distal end 46 of the cable 50 and the actuator cap 42 is made by fixing the attachment device 52 to the actuator cap 42, and then wrapping slack in the cable 50 around the outer top surface of the actuator cap 42. The outer top surface of the actuator cap 42 includes the slotted groove 54 along the top of the actuator cap 42. When the cable 50 is wrapped around the outer slotted groove 54 of the actuator cap 42, a smaller boss diameter 62 of the actuator cap 42 is mated with a mating diameter 64 of the actuator head 18. Thus, the actuator cap 42 may rotate with respect to the actuator head 18, through the pivotal connection between the smaller boss diameter 62 and the mating diameter 64. A compression force applied to the actuator cap 42 and the actuator head 18 seats a snap interface and completes assembly of the tool 14.

Figure 3C:
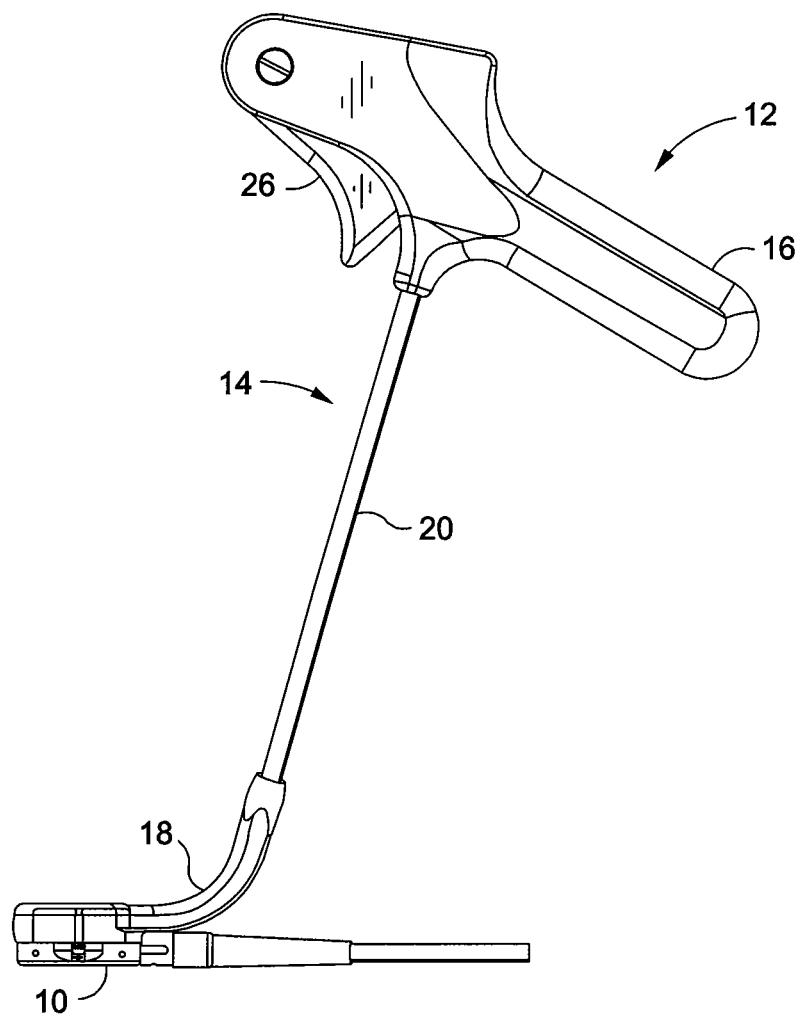
FIG. 3C illustrates a side view of the tool according to an embodiment of the present invention.

FIG. 3C illustrates a side view of the system 12, including the assembled tool 14 engaged with an access port 10.

Figure 3D:
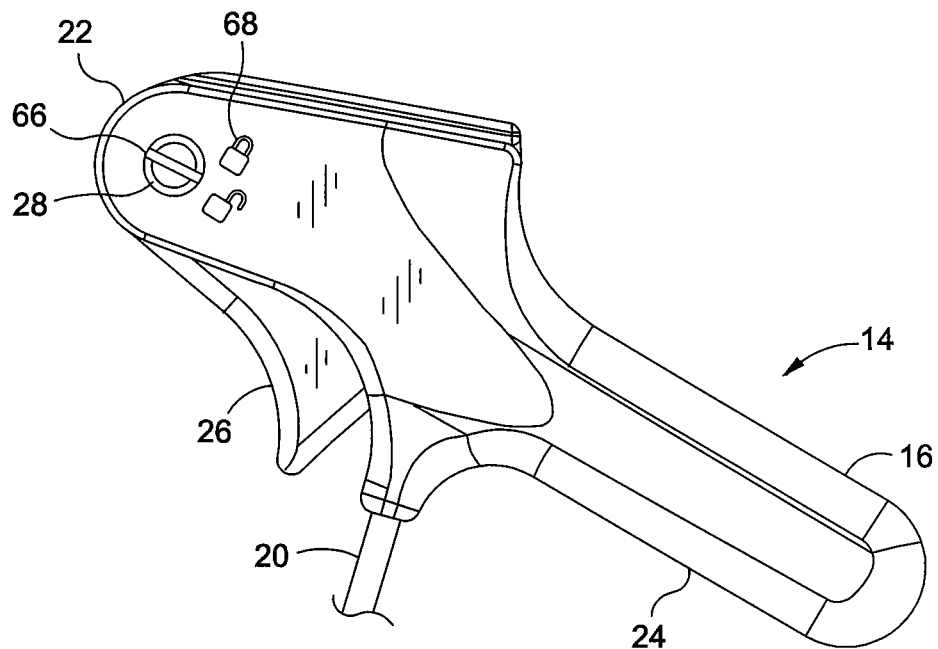
FIGS. 3D and 3E each illustrate a side, close-up view of the tool's handle according to an embodiment of the present invention.

FIG. 3D illustrates an aspect of the tool's 14 operation, related to the use of the trigger 26. To operate the tool 14, a user grips the grip portion 24 and squeezes the trigger 26 in a direction towards the top of the handle 16. As shown in FIG. 3D, the pin 28 may include a notch 66, or pointer, that points to a status indicator 68. The notch 66 points to an indicator 68 that indicates whether the access port 10 is in an undeployed, or unlocked position, or is in a deployed, or locked position. Accordingly, if the trigger 26 has not yet been pressed, the notch 66 points to the unlocked status indicator 68.

Figure 3E:
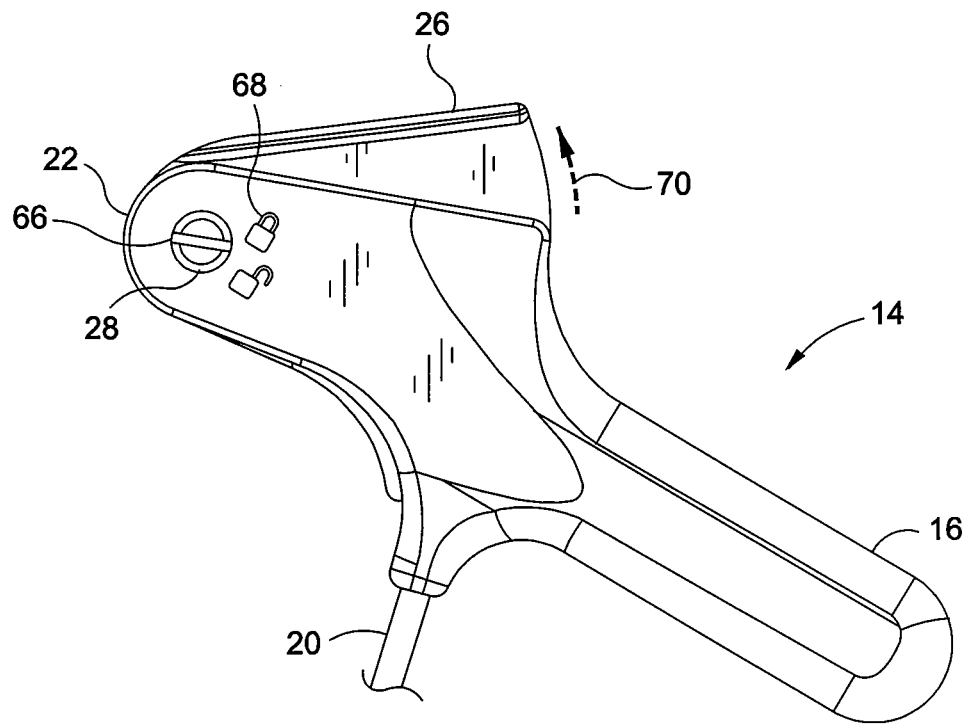

FIG. 3E illustrates the tool 14 in a deployed state after the trigger 26 has been pressed in the direction indicated by the arrow 70. Because the pin 28 is pivotally coupled to the apertures 30 (shown in FIG. 3B), the trigger 26 rotates when it is squeezed. In this configuration, the notch 66 points to an indicator 68 indicating the access port 10 is locked, or deployed.

In operation, when the trigger 26 is pressed in the direction indicated by the arrow 70, the ball receiving structure 58 pulls on the ball 47 of the cable assembly 40. The cable 50 is then pulled in a direction towards the handle 16, which rotates the actuator cap 42. The distal portion 46 of the cable assembly 40, wrapped around the slotted groove 54, assures the translational movement of the cable 50 up or down along inside the interior of the extension tube 20 is converted to a rotational movement of the actuator cap 42. To return the tool 14 to the system shown in FIG. 3D, the user presses the trigger 26 in a direction opposite to arrow 70. Because the cable 50 is made of a stiff, or rigid material, the cable 50 will rotate the actuator cap 42 back to its initial position. The push/pull connection between the trigger 26 and actuator cap 42 offers an improved tactile sense for the user. In addition, the present design further does not require costly material for manufacture, for example, PEEK.

Figure 4A:
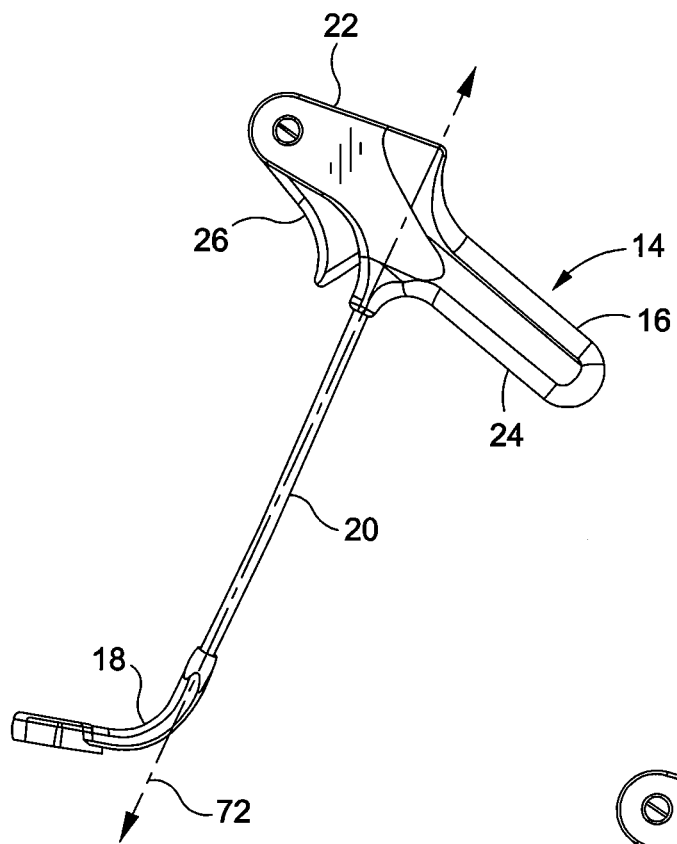
FIGS. 4A and 4B each illustrate a side view of the tool according to an embodiment of the present invention.
Figure 4B:
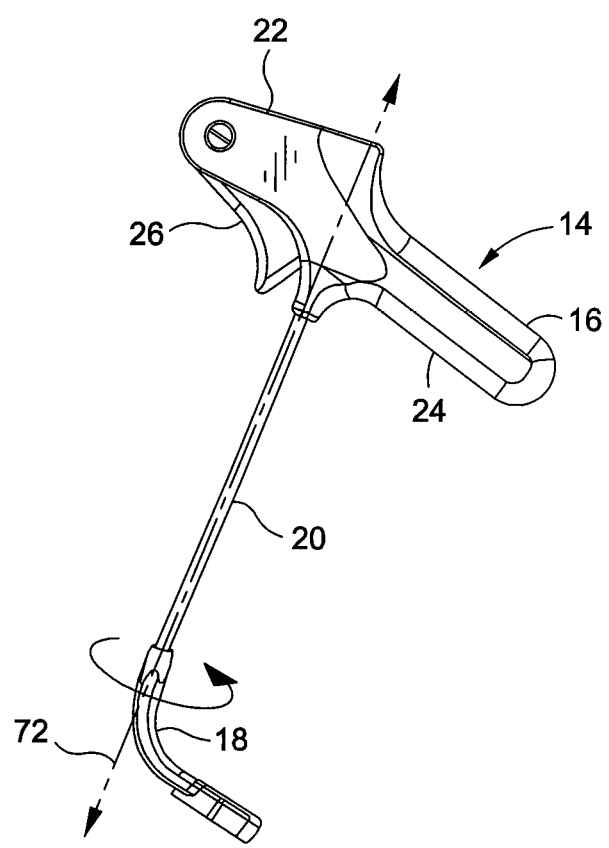

FIGS. 4A and 4B illustrate the actuator head 18 being pivotal with respect to the handle 16. As described above in relation to FIG. 3B, either the actuator head 18, or the extension tube 20, or both, may be pivotally coupled to the handle 16. In one embodiment, as discussed above, the extension tube 20 includes a pivot device 31 (shown in FIG. 3B) that couples to the handle 16, to allow the extension tube 20 to rotate with respect to the handle 16. In one embodiment, the radius tube 36 may include a similar pivot device attaching the radius tube 36 to the extension tube 20. Rotation of the extension tube 20 or rotation of the radius tube 36 will allow the actuator head 18 to rotate. In addition, in one embodiment discussed in relation to FIG. 3B, either the radius tube 36 or the extension tube 20 may be rotated, or pivoted in multiple dimensions with respect to the handle 16.

The extension tube 20 may define a lateral axis 72 that the actuator head 18 may rotate around. Depending on the configuration of the tool 14, the actuator head 18 may be configured to rotate 90 degrees about the axis 72, 180 degrees about the axis 72, or 360 degrees about the axis 72. In addition, a friction mechanism or locking mechanism may be used to hold the rotated actuator head 18 in position after it has been rotated. In one embodiment, the friction between the pivot device 31 and the mating slot may be sufficient to hold the actuator head 18 in position after it has been rotated.

The ball 47 located at the proximal end 44 of the cable assembly 40 allows the cable assembly 40 to rotate with the actuator head 18. A shape of a cavity of the ball receiving structure 58 corresponds to the shape of the ball 47 and allows the ball 47 to rotate within the cavity. The ball 47 of the cable assembly 40 therefore aids, or enables the actuator head 18 to pivot with respect to the handle 16.

The actuator head 18 pivots to allow a user to have a rotational degree of freedom when inserting the access port 10 into a patient's body. The rotating actuator head 18 allows the user to insert the access port 10 in multiple positions, yet retain the same grip on the handle 16. This feature may be beneficial if the access port 10 will be attached to a portion of the patient's body that is difficult to access. In general, the rotational feature facilitates greater manipulation and positioning of the access port 10 during implantation.

Figure 5A:
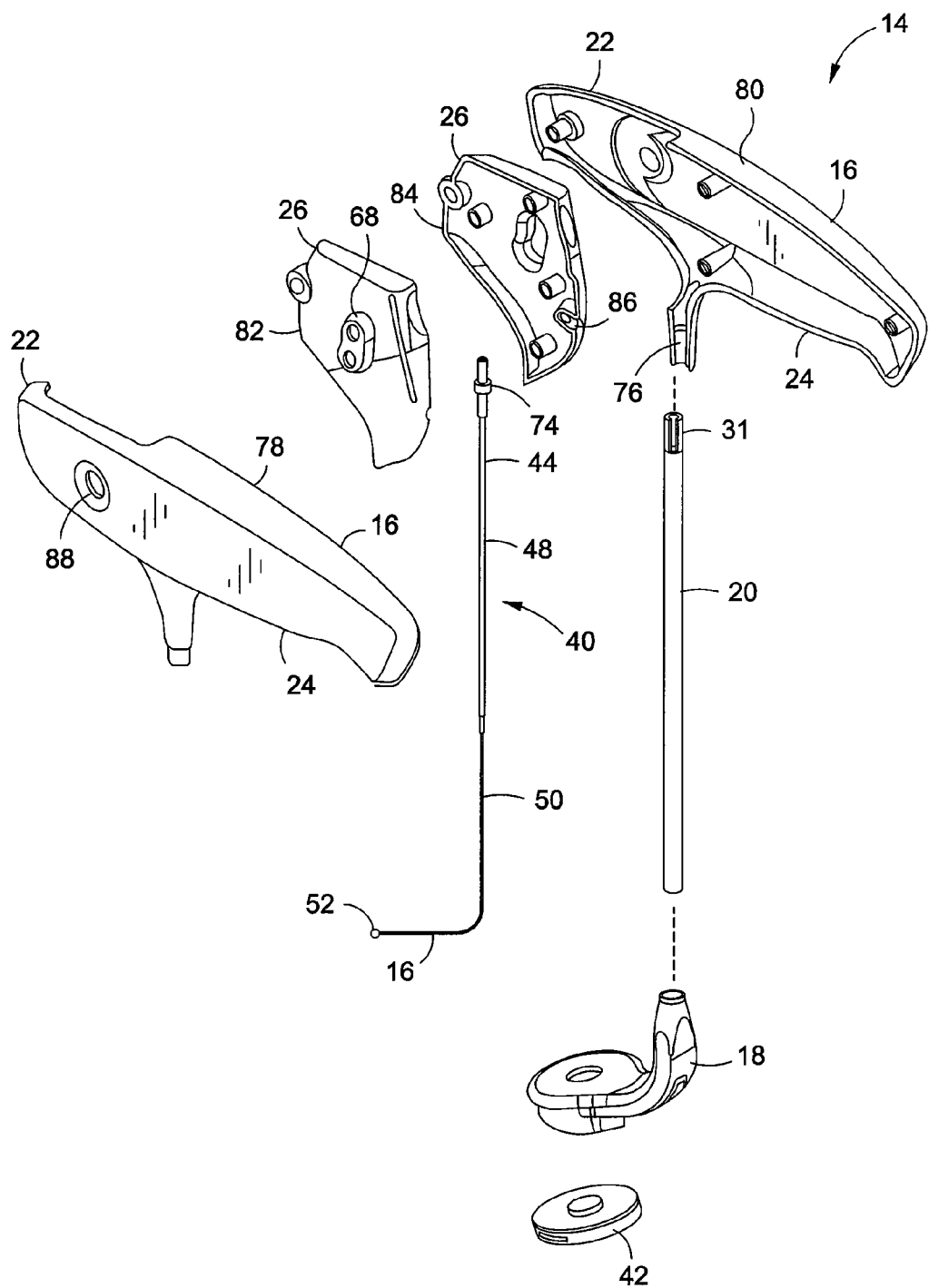
FIG. 5A illustrates an exploded perspective view of the tool according to an embodiment of the present invention.

FIGS. 5A-5E illustrate an embodiment of the present invention including design variations from the embodiments shown in FIGS. 3A-3E. In particular, FIG. 5A illustrates an exploded view of the present invention including a two part 78, 80 handle 16 structure that is combined together through columns, screws, fasteners, or the like. The two part handle 16 encloses a two part 82, 84 trigger 26 that is similarly combined with columns, screws, fasteners, or the like. The two part trigger 26 encloses a plug 74, a ball device, or cylindrical shaped device positioned at the proximal end 44 of the cable 50. The plug 74 is housed within the plug receiving structure 86. Similar to the operation of the ball 47 and the ball receiving structure 58 shown in FIG. 3B, the plug 74 and the plug receiving structure 86 are shaped to allow, or enable the actuator head 18 to rotate. The ball 47 (shown in FIG. 3B) and the plug 74 represent generally equivalent attachment mechanisms for the cable assembly 40. In addition, the mating slot 76 (here more clearly visible than in FIG. 3B) encloses the pivot device 31 of the extension tube 20. Furthermore, in this embodiment, an aperture 88 is positioned to allow the status indicator 68 to be visible when the tool 14 is either in the deployed or undeployed state.

FIG. 5B illustrates a side view of the tool 14, shown in FIG. 5A, in the undeployed position. The status indicator 68 accordingly displays an undeployed, or unlocked indicator, as shown in FIG. 5C. FIG. 5D illustrates a side view of the tool 14 in the deployed position. The status indicator 68 accordingly displays a deployed, or locked indicator, as shown in FIG. 5E.

Figure 6A:
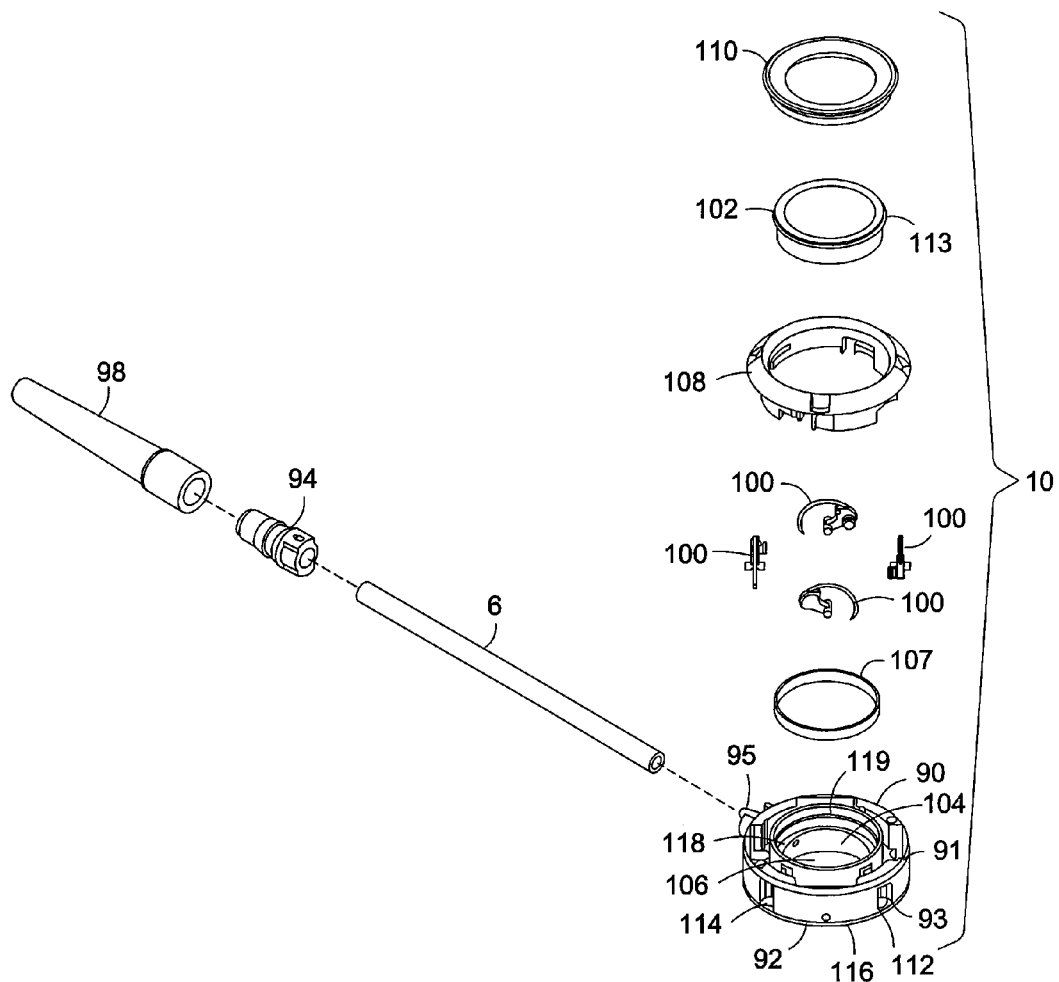
FIG. 6A illustrates an exploded perspective view of the access port according to an embodiment of the present invention.

FIG. 6A illustrates an access port 10 shown in an exploded view. The access port 10 in this embodiment generally comprises a housing 90, having a generally cylindrical shape. The housing 90 has a top portion 91 and a bottom portion 93. The bottom portion 93 includes a base 92 fixed to the housing 90, and comprising a bottom surface of the housing 90. The base 92 provides a generally flat surface at the bottom of the housing 90. The base 92 may be made from injection molded plastic, or the equivalent. The base 92 may further include an overmolded metal needle guard to prevent a syringe needle from penetrating and passing through the bottom portion 93 of the housing 90.

Figure 6B:
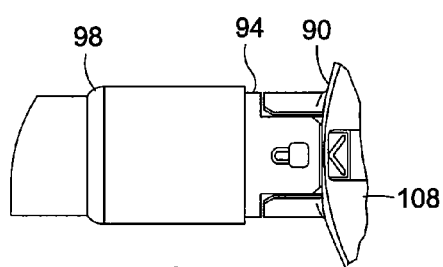
FIG. 6B illustrates a close-up view of a tube connector according to an embodiment of the present invention.
Figure 6C:
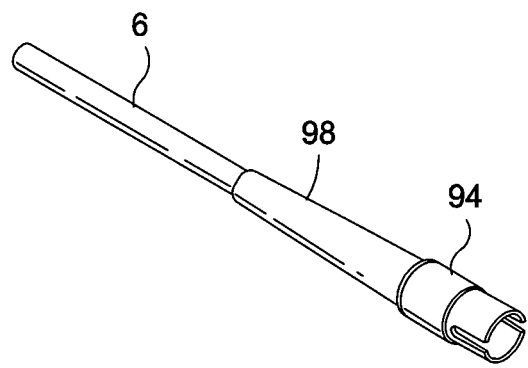
FIG. 6C illustrates a perspective view of a tube connector according to an embodiment of the present invention.

The housing 90 includes an access port connector 95 at one side of the housing 90. The access port connector 95 is configured to engage a tube 6 connecting from the access port 10 to the gastric band 4 (as shown in FIG. 1). A tube connector 94 may be connected to an end of the tube 6, and fixed to the access port connector 95, to secure engagement of the tube 6 with the access port housing 90. The inner diameter of tube connector 94 compresses tube 6 onto the port connector 95 to ensure sealing. The tube connector 94 may include a locking indicator, shown in FIG. 6B, indicating when the tube 6 has been properly engaged and locked with the housing 90. The actuator 108 may have a similar indicator displaying a locked position. The tube connector 94 may additionally have a locking engagement mechanism, for example a friction element or a mechanical element to lock the tube 6 to the housing 90. The tube connector 94 may comprise injection molded plastic or molded silicone, or both, or the like. A strain relief element 98 may additionally be placed over a portion of the tube 6. One embodiment of the tube connector 94, shown in FIG. 6C, includes a split-cylinder shape, and does not include the locking indicator shown in FIG. 6B.

Figure 14:
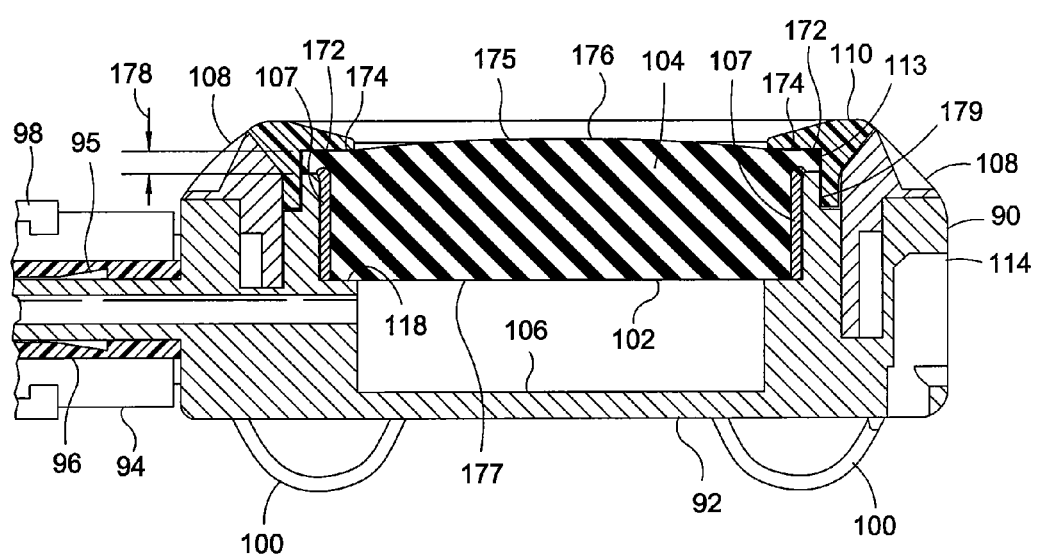
FIG. 14 illustrates a side, cross sectional view of the access port according to an embodiment of the present invention.

The access port housing 90 generally may define two interior cavities. One interior cavity includes the fluid chamber 106 (shown more clearly in FIG. 14). Another interior cavity includes the central cavity 104 (shown more clearly in FIG. 14). The fluid chamber 106 stores fluid transferred to the gastric band 4 through the tube 6 (as shown in FIG. 1). The septum 102 is placed within the central cavity 104 and is placed over the fluid chamber 106. The septum 102 substantially opposes the base 92. A septum counter bore 118, or ridge, seats the septum 102 over the fluid chamber 106. A compression ring 107 is placed around the septum 102 to hold the septum 102 in place. An upper rim 113 of the septum 102 is positioned over an upper ridge 119 of the housing 90. A pulpation ring 110 (equivalently described as a locking ring) is further placed over the septum 102 to hold the septum 102 in place and protect the fluid chamber 106 from leakage, as further described in relation to FIG. 14. The pulpation ring 110 locks around a portion of the housing, as shown in FIG. 14. An actuator 108 is additionally placed over a top portion 91 of the housing 90. It is noted that each device placed in within the interior cavities of the housing has a generally cylindrical shape, to conform to the shape of the cavities. Furthermore, each device placed within the interior cavities is positioned substantially concentric with one another.

Figure 7:
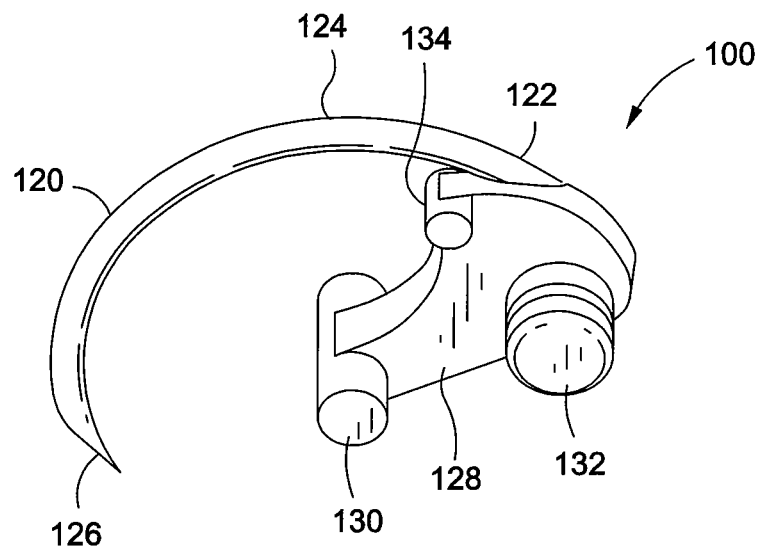
FIG. 7 illustrates a perspective view of an anchor assembly according to an embodiment of the present invention.

The access port 10 further comprises a plurality of anchor assemblies 100 (sometimes hereinafter referred to simply as anchor 100). Referring to FIG. 7, the anchor assembly 100 may be a composite element, for example, made of at least two different materials. The anchor assembly 100 includes a wire portion 124 and a molded portion 128. The wire portion 124 may comprise stainless steel, or the equivalent, and the molded portion may comprise, for example, a plastic or polymer, or the equivalent. In one embodiment, the molded portion 128 is molded around the wire portion 124. In one embodiment, the molded portion 128 is overmolded around the wire portion 124.

In one embodiment, each anchor assembly 100 is made of a bioresorbable material. A portion of the anchor assembly 100 or the entirety of the anchor assembly may be made of one or more bioresorbable material. For example, the wire portion 124, or the molded portion 128, or both, may be made of a bioresorbable material. The bioresorbable material serves to increase the biological compatibility between the anchor 100 and the body tissue.

The wire portion 124 may include a distal portion 120 and a proximal portion 122. The distal portion 120 may include a distal tip 126 structured to penetrate and engage tissue. The distal tip 126 represents the end point of the wire portion 124. The wire portion 124 may have a generally curved shape, to allow the anchor 100 to hook into, and engage the tissue located below the access port 10. In addition, the wire portion 124 may have a generally circular cross section, to reduce friction with the tissue, and to reduce the total cross sectional surface area contacting the tissue. The circular cross section may extend over the length of the wire portion 124, until the wire portion 124 terminates in the distal tip 126. The circular cross section is formed because the wire portion 124 may be considered simply as a curved needle. In addition, the circular, constant cross section may be additionally beneficial if the wire is formed from, for example, stainless steel. The stainless steel wire may be work hardened, giving it a higher strength than wrought material. The circular cross section may therefore comprise an improvement over, for example, an anchor having a tapered shape.

The proximal portion 122 includes the molded portion 128 molded, or overmolded to the proximal portion 122 of the wire portion 124. The molded portion 128 may include a pivot axle 130 with an axis that extends in a direction substantially perpendicular to a plane of rotation of the wire portion 124. Further, the molded portion 128 may comprise an actuator pin 132 also extending in a direction substantially perpendicular to a plane of rotation of the wire portion 124. The actuator pin 132 is spaced apart from the pivot axle 130, preferably at a far, or the furthest distance available on the molded portion 128 from the pivot axle 130. Thus, the actuator pin 132 may be spaced at one end of the molded portion 128 from the pivot axle 130. In addition, the molded portion 128 may comprise a deploy pin 134 extending in a direction substantially perpendicular to a plane of rotation of the wire portion 124.

The deploy pin 134 is spaced apart from the actuator pin 132 and the pivot axle 130. The actuator pin 132 and deploy pin 134 may be formed during the molding process of the molded portion 128, such that they represent a singular, continuous unit with the molded portion 128. In the embodiment shown in FIG. 7, the actuator pin 132, the deploy pin 134, and the pivot axle 130, all have a generally cylindrical shape extending outwards from the surface of the molded portion 128. In addition, the actuator pin 132, the deploy pin 134, and the pivot axle 130, all have curved surfaces that allow the actuator 108 to pivotally engage the actuator pin 132 and the deploy pin 134. In one embodiment, the actuator pin 132 and deploy pin 134 may have various equivalent shapes, may extending in various equivalent directions, and may not necessarily comprise a continuous unit with the molded portion 128.

Referring back to FIG. 6A, the assembly of the access port 10 begins with the insertion of the anchor assemblies 100 into the housing 90. The anchor assemblies 100 are coupled to the housing 90 by their pivot axles 130, which snap into place. An axle mating feature 116 positioned along a side of the housing 90 retains one end of the pivot axle 130. A portion of the housing 90 retains the other end of the pivot axle 130. The compression ring 107 is pressed into place within the central cavity 104 to reinforce the plastic housing 90 for the interference fit with the pulpation ring 110 (more clearly shown in FIG. 14). The septum 102 is lowered into place within the compression ring 107 to form a covering over the fluid chamber 106. The actuator 108 is then positioned concentric with the housing 90, is engaged with the housing 90, and is lowered to engage the anchor assemblies 100. Engagement with the anchor assemblies 100 may be made at at least one of four locations. Preferably, the actuator 108 is engaged with the anchor assemblies 100 when they are in a half-deployed position, to allow for easy engagement between the actuator 108, the actuator pin 132 and the deploy pin 134. The pulpation ring 110 is then positioned concentric with the housing 90. A compression force is applied to the pulpation ring 110 until the inner diameter of the pulpation ring snaps over an outer diameter of a portion of the housing 90, as more clearly shown in FIG. 14.

Figure 8A:
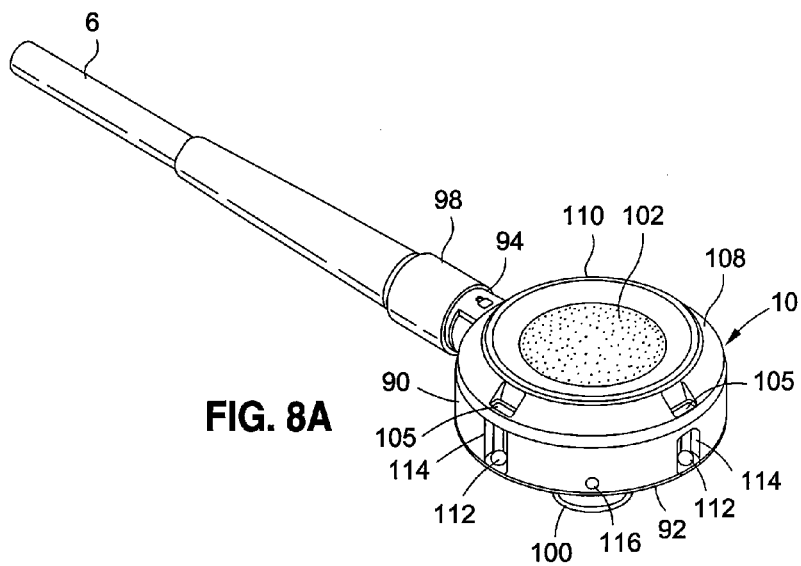
FIG. 8A illustrates a perspective view of the access port according to an embodiment of the present invention.
Figure 8B:
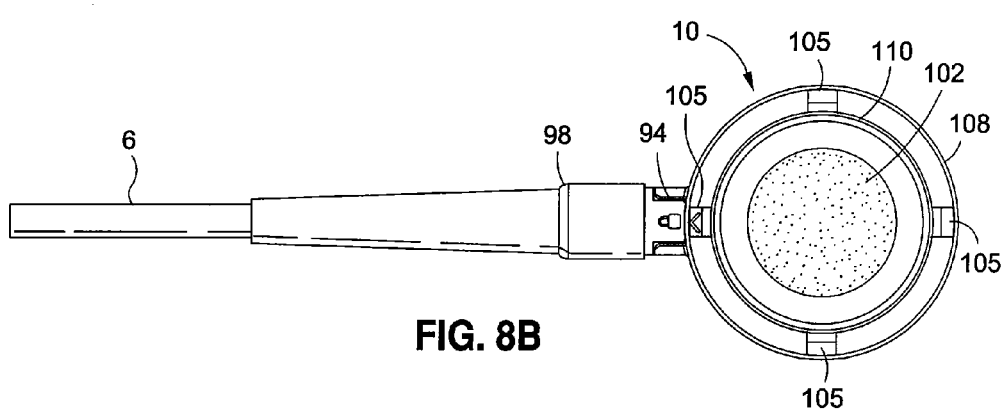
FIG. 8B illustrates a top view of the access port according to an embodiment of the present invention.
Figure 8C:
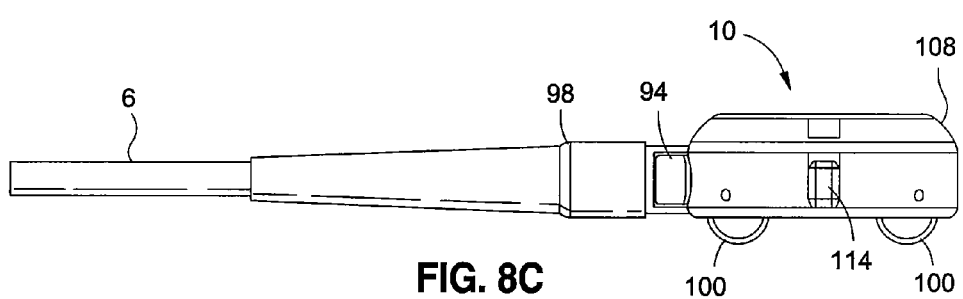
FIG. 8C illustrates a side view of the access port according to an embodiment of the present invention.

FIG. 8A illustrates a perspective view of the assembled access port 10. FIGS. 8B and 8C illustrate respective top and side views of the access port 10. FIGS. 8A-8C illustrate additional features of the access port 10, including suture holes 112 placed along the side of housing 90 and side cuts 114 placed on the side the housing 90. The suture holes 112 allow a physician to suture the access port 10 to a patient's body, rather than utilizing the anchors 100. The suture holes 112 may also be used in addition to the anchors 100. The suture holes 112 may comprise three holes spaced, for example, 90 degrees apart. Furthermore, the side cuts 114 are used for engagement with the tool 14, as further discussed in relation to FIGS. 15A-22B. FIG. 8A additionally displays actuator side cuts 105 placed along a periphery of the actuator 108. The actuator side cuts 105 are used as an engagement mechanism with the tool 14, and specifically the actuator cap 42, as further discussed in relation to FIGS. 15A-22B.

Figure 9A:
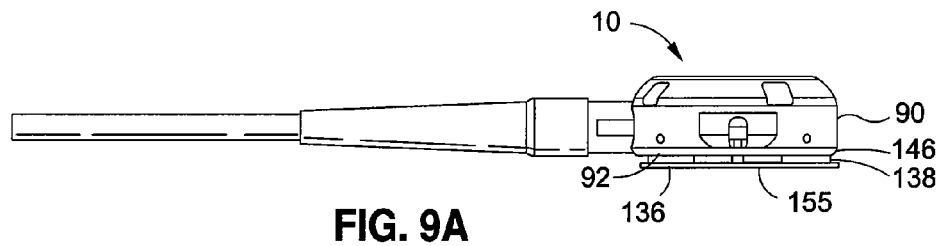
FIGS. 9A, 9C, 9F, 9H and 9J each illustrate a side view of the access port according to an embodiment of the present invention.
Figure 9B:
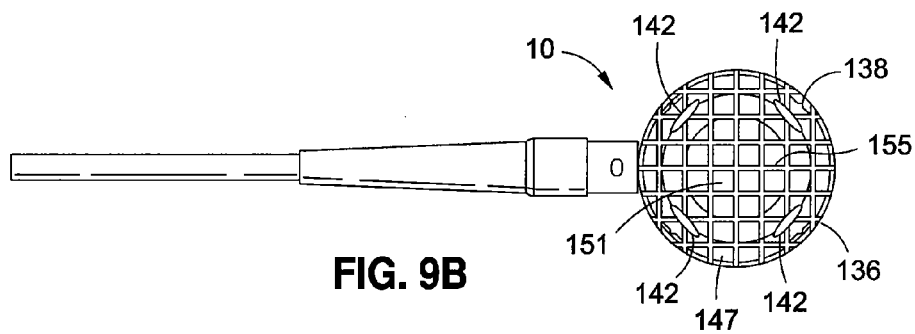
FIGS. 9B, 9D, 9G, 9I and 9K each illustrate a bottom view of the access port according to an embodiment of the present invention.

Referring now to FIGS. 9A and 9B, one embodiment of the present invention may include an attachment material, for example, a mesh member 136 disposed along at least a portion of the base 92 for encouraging tissue ingrowth or tissue engagement after the access port 10 has been implanted in the patient. In the embodiment shown in FIGS. 9A and 9B, the mesh member 136 does not extend out beyond an outer circumference 146 or outer extent of the access port 10. The mesh member 136 may have a generally web-shape or checkerboard shape, including a plurality of structures that cross in varied directions to form a series of intersections and spaces 139b (shown in FIG. 9D) in between those intersections. In addition, the mesh member 136 may have a microstructure much smaller than shown in FIG. 9B, or may have a circular, triangular, or other equivalent mesh structure. In one embodiment, the mesh member 136 may comprise merely a porous material.

The mesh member 136 may encourage local tissue around the access port 10 to engage with the access port 10 after the access port 10 has been applied. The mesh member 136 aids to secure the access port 10 in place on the patient's tissue. In addition, the mesh member may aid to form a biological seal, or a dermal interface, around the interface between the tissue and the access port 10. In addition, the mesh member 136 may prevent the local tissue from rejecting the access port 10 and may decrease the chance of medical complications related to the access port 10.

Furthermore, a portion of the mesh member 136 may be used as an attachment point to suture, staple, or otherwise lock the access port 10 to the patient's body.

The mesh member 136 may be made of a bioresorbable material, such as silk, or the like, or may be made of a non-resorbable material such as polypropylene, or the like. In addition, the mesh member 136 may be made of a blend of both bioresorbable materials and non-resorbable materials such as a Covidien mesh, or the like.

The mesh member 136 may be used to engage bodily tissue in conjunction with either sutures extending from the suture holes 112 or with use of the anchor assemblies 100, or both. If the anchor assemblies 100 are used to fix the access port 10 to bodily tissue, the mesh member 136 may include apertures 142 appropriately sized to allow a portion of the anchor assemblies 100 to pass through the mesh member 136. In addition, the mesh member 136 may be sized to allow the anchor assemblies 100 to pass through the mesh member 136 without contacting or damaging the mesh member 136. If the mesh member 136 is appropriately sized, no apertures 142 may be needed.

Figure 9C:
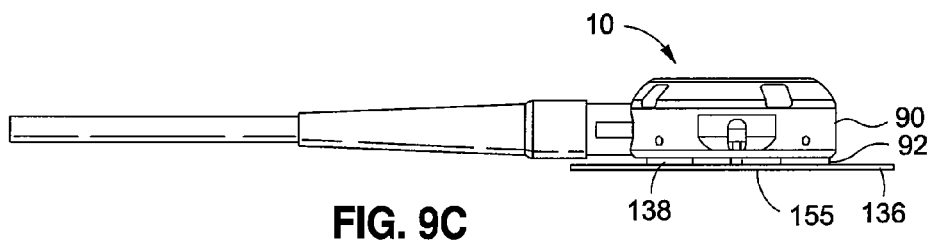
Figure 9D:
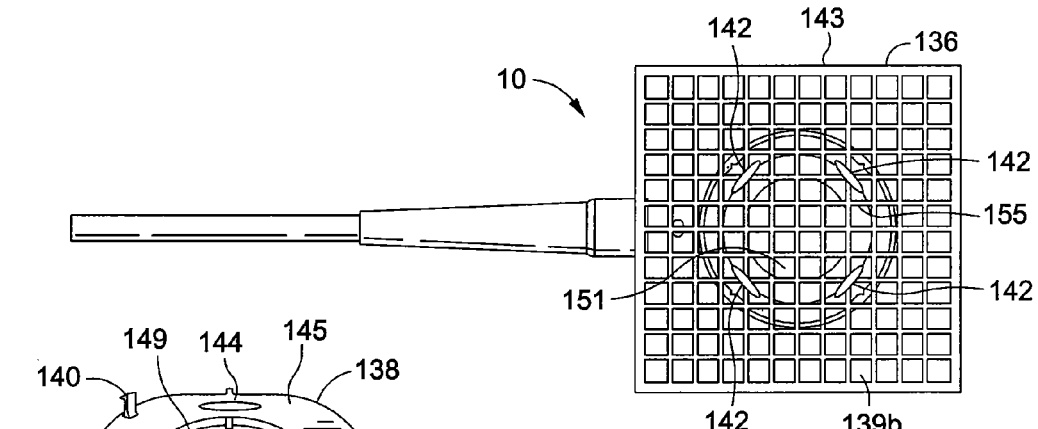
Figure 9E:
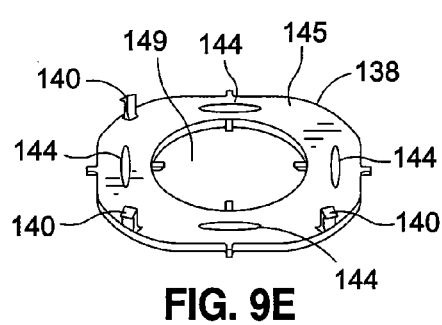
FIG. 9E illustrates a perspective view of a mesh ring according to an embodiment of the present invention.

The mesh member 136 may be fixed to the base 92 of the housing 90, through a mesh ring 138, shown more clearly in FIG. 9E. The mesh ring 138 may have a generally disk-like or plate-like shape that may have a central aperture 149. The mesh ring 138 may have a top surface 145 and a bottom surface 147 (shown in FIG. 9B), wherein the top surface 145 is connected to the base 92 of the housing 90, at a bottom surface 151 of the base 92. The bottom surface 147 of the mesh ring 138 may be connected to a top surface 153 (referred to in FIG. 9F) of the mesh member 136. The mesh ring 138 may be configured to not extend beyond an outer circumference 146 or outer extent of the access port 10.

The mesh ring 138 may additionally include a plurality of apertures 144 that allow the anchor assemblies 100 to pass through the mesh ring 138 and engage tissue. These apertures 144 may be excluded if the anchor assemblies 100 are not used to fix the access port 10 to the patient. In addition, the mesh ring 138 may include a plurality of columns 140 that engage the base 92 of the housing 90. If the suture holes 112 are not used to engage the access port 10 with bodily tissue, the plurality of columns 140 may engage with the suture holes 112. The plurality of columns 140 may equivalently engage to other portions of the access port housing 90. Other equivalent attachment means may also be used.

The mesh member 136 may be attached to the mesh ring 138 mechanically or by physically wrapping or tying the mesh member 136 to the mesh ring 138. In addition, a latching mechanism may be used to attach the mesh member 136 to the mesh ring 138.

The mesh ring 138 allows the physician, at the time the access port 10 is inserted, to determine whether or not to include the mesh member 136. The detachable mesh ring 138, removably fixed to the base 92, allows a physician to choose whether or not to detach the mesh ring 138. In addition, the mesh ring 138 may provide clearance for bodily tissue to better engage the mesh member 136, by providing more distance between body tissue and the base 92. In one embodiment, the mesh ring 138 may be permanently fixed to the base 92 (e.g., an embodiment where the mesh ring 138 is not detachable from the base 92).

FIGS. 9C and 9D illustrate an embodiment of the present invention utilizing the mesh member 136 and mesh ring 138, where the mesh member 136 is welded to the mesh ring 138. The welding process may include an ultrasonic welding process, and may be used as an alternative or in combination with the attachment methods disclosed in relation to FIGS. 9A and 9B. In addition, the mesh ring 138 may be adhered to the bottom surface 151 of the base 92, for example, by gluing the mesh ring 138 to the base 92, or through other equivalent means. In addition, in this embodiment, the mesh member 136 extends beyond the outer circumference 146 or outer extent of the access port housing 90. The portion 143 of the mesh member 143 extending beyond the base 92 may extend outwardly from and substantially circumscribe the base 92, or may extend only partially around the base 92. In addition to an ultrasonic welding process, the mesh member 136 may be attached to the ring 138 through other equivalent attachment means. The mesh member 136 extends beyond the outer circumference 146 or outer extent of the access port housing 90 to allow a physician to cut the mesh member 136 to an appropriate size before implantation into a patient. In addition, the mesh member 136 may extend beyond the outer circumference 146 of the access port 10 to allow a physician to more easily suture or attach the mesh to a patient.

Figure 9F:
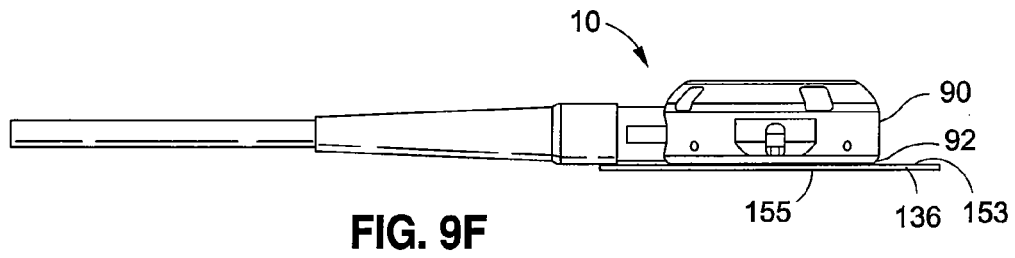
Figure 9G:
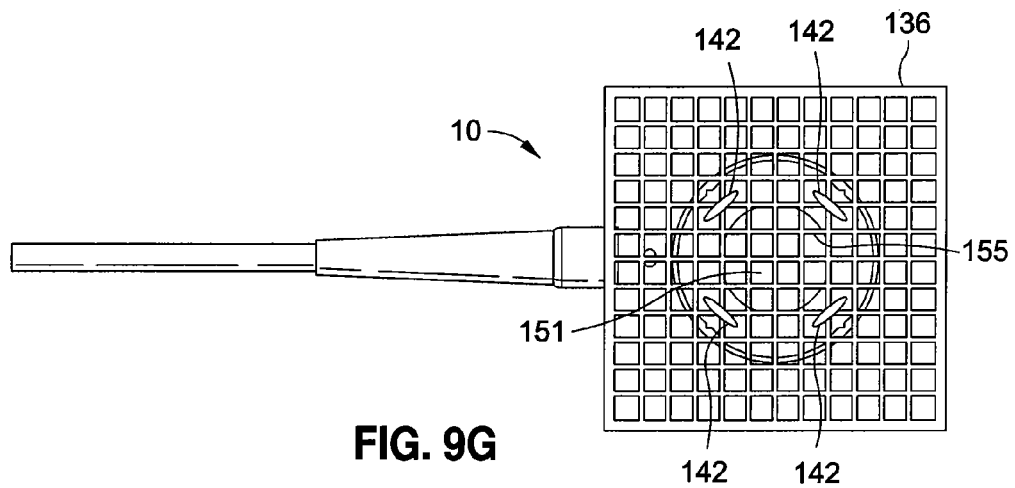

FIGS. 9F and 9G illustrate one embodiment of the present invention wherein the mesh member 136 is attached directly to the base 92 without the use of the mesh ring 138. In this embodiment, the mesh member 136 may be ultrasonically welded to the base 92 of the access port 10, or may be attached through other equivalent means. Other equivalent means may include crimping or folding a portion of the mesh member 136 to a portion of the base 92. In this embodiment, a top surface 153 of the mesh member 136 is fixed directly to a bottom surface 151 of the base 92. A bottom surface 155 of the mesh member 136 contacts the body tissue.

Figure 9H:
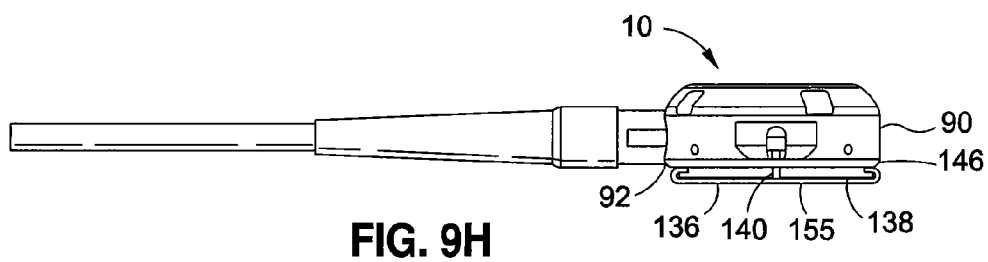
Figure 9I:
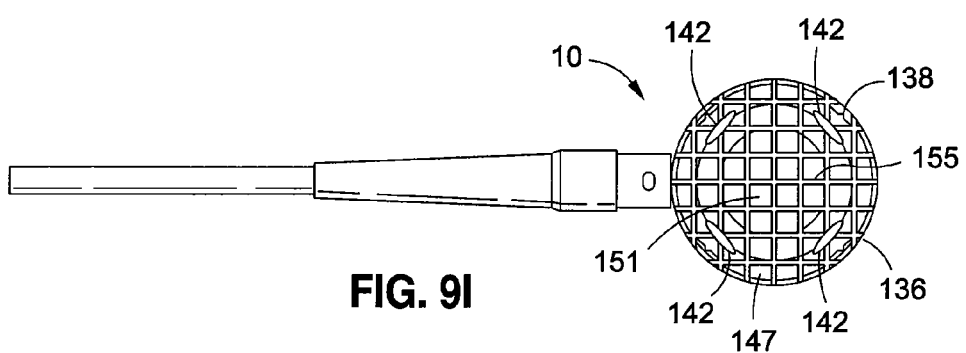

FIGS. 9H and 9I illustrate an embodiment of the present invention wherein a portion of the mesh member 136 may wrap or fold around the outer circumference of the mesh ring 138. In this embodiment, a portion of the mesh member 136 is sandwiched between the bottom surface 151 of the base 92 and the top surface 153 of the mesh ring 138 (shown in FIG. 9F). This is a press fit, where the mesh member 136 is not welded or bonded to the base 92. The portion of the mesh member 136 that wraps around the outer circumference of the mesh ring 138 is then locked between the base 92 and the mesh ring 138, holding it in place. The portion of the mesh member 136 that wraps around the mesh ring 138 may be firmly or loosely sandwiched between top surface 153 of the mesh ring 138 and the bottom surface 151 of the base 92.

Figure 9J:
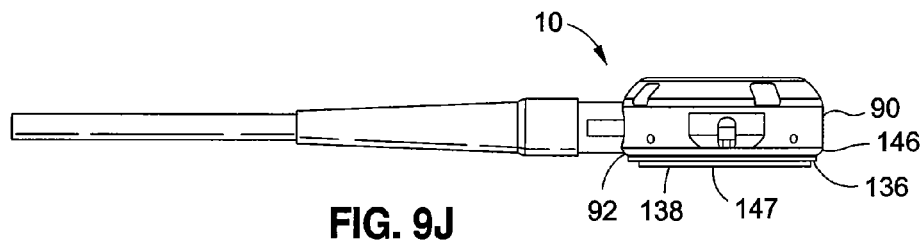
Figure 9K:
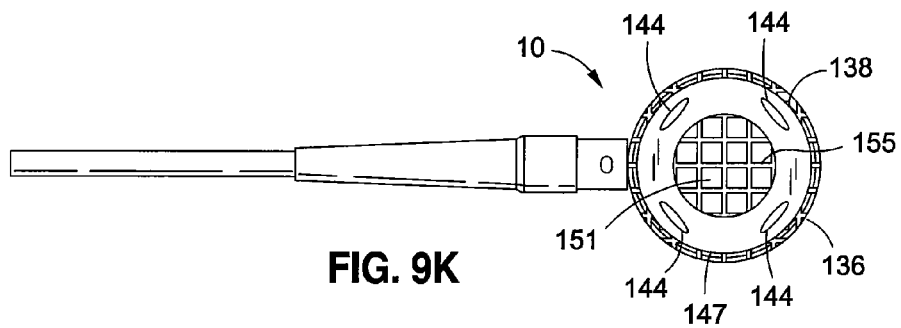

FIGS. 9J and 9K illustrate the mesh member 136 may be entirely sandwiched between the top surface 153 of the mesh ring 138 and the bottom surface 151 of the base 92. In other words, the mesh member 136 may be held in place by the mesh ring 138 positioned on the bottom surface 147 of the mesh member 136. A portion of the mesh ring 138 would fix to the bottom surface 151 of the base 92 by having an attachment mechanism pass through the mesh member 136.

In one embodiment, the mesh member 136 may be integrally molded into or as part of the base 92 of the access port 10. In this embodiment, the mesh member 136 and the base 92, particularly the bottom surface 151 of the base 92, may be molded as one piece. In addition, the mesh member 136 may be overmolded on to the base 92, or a portion of the base 92. The mesh member 136 and base 92 may be made of different materials or the same materials, particularly the materials discussed above in relation to FIGS. 9A and 9B. If the mesh member 136 is overmolded to the base 92, it may be easier to form the base 92 and mesh member 136 from different materials.

Figure 9L:
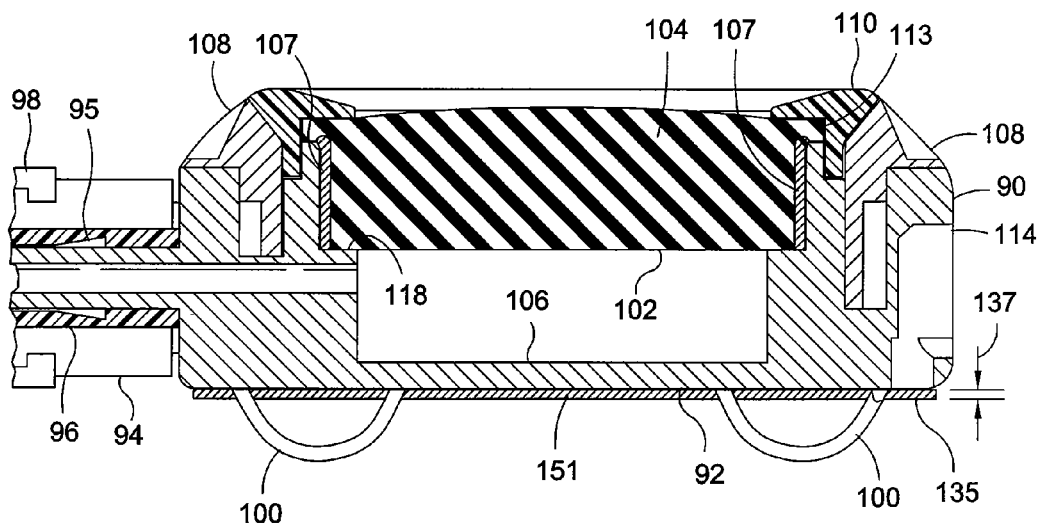
FIG. 9L illustrates a side, cross sectional view of the access port according to an embodiment of the present invention.

In one embodiment, the bottom surface 151 of the base 92 may be coated with a bioresorbable material, to encourage biological compatibility between the base 92 and the body tissue. FIG. 9L illustrates a coating 135 may cover the entirety of the bottom surface 151 of the base 92, or only a portion of the bottom surface 151 of the base 92. A thickness 137 of the coating 135 may be even, or may vary along the bottom surface 151 of the base 92. The coating 135 may be deposited through a process including a spraying process, dipping process, molding process, wiping process, or other equivalent means of attaching the bioresorbable material to the base 92. The coating thickness 137 may vary between approximately 0.001 inches and 0.25 inches. The bioresorbable material serves to form a biological seal between the access port 10 and the body tissue, and to encourage compatibility between the access port 10 and the body tissue.

Similarly, in one embodiment, the base 92 itself (particularly the bottom surface 151 of the base 92), may be made entirely or partially from a bioresorbable material. Thus, a portion of the bottom surface 151 of the base 92 or the entirety of the bottom surface 151 of the base 92 may be made of a bioresorbable material. The bioresorbable base 92 may be formed through a process including a molding process, a forming process, a stamping process, or other equivalent means of forming a base 92 partially or entirely formed of bioresorbable material to the base 92. The bioresorbable base 92, as discussed above in relation to the coating of bioresorbable material, serves to form a biological seal between the access port 10 and the body tissue, and to encourage compatibility between the access port 10 and the body tissue.

Figure 10A:
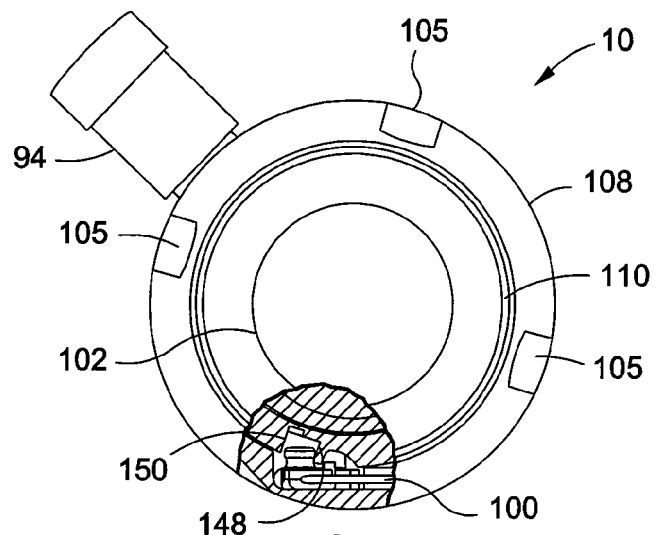
FIGS. 10A and 10D each illustrate a top view of the access port according to an embodiment of the present invention.

FIGS. 10A-13E illustrate the deployment of the anchor assemblies 100 according to one embodiment of the present invention. FIG. 10A illustrates a top view of the access port 10 with the actuator 108 positioned at an angle with respect to the access port housing 90 and at an angle with, for example, the tube connector 94. The initial, undeployed, angle may be offset 64 degrees from the deployed angle. In addition, the initial configuration represents the position of the tool 14 and the access port 10 in the retracted, undeployed, or unlocked state.

Figure 10B:
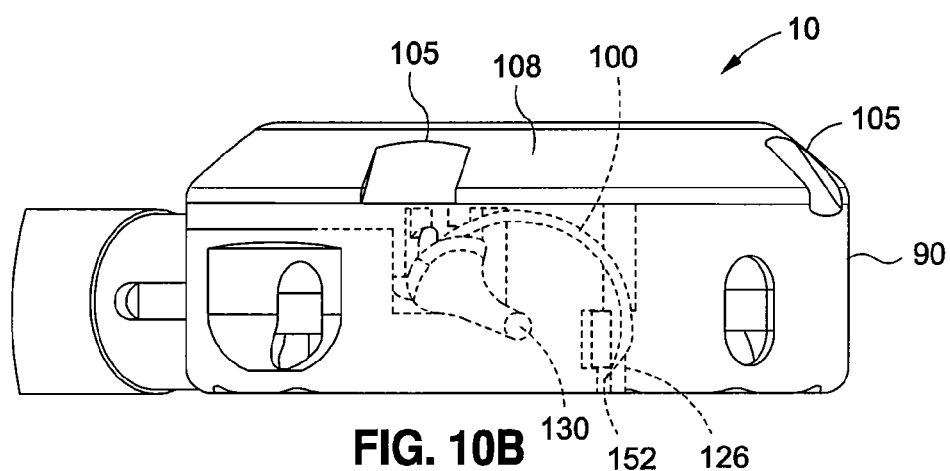
FIG. 10B illustrates a side view of the access port according to an embodiment of the present invention.

FIG. 10B illustrates a side view of an anchor assembly 100 housed within the access port housing 90. The anchor assembly 100 is shown in the retracted position: a position where the distal tip 126 of the anchor assembly 100 has not yet exited the base 92 of the access port 10 through an aperture 152.

Figure 10C:
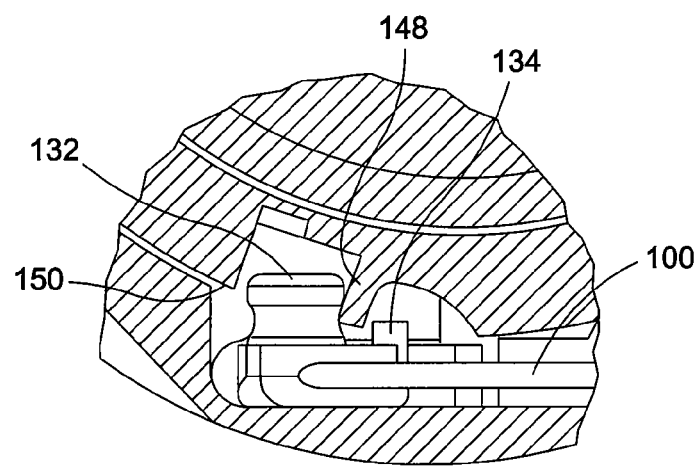
FIG. 10C illustrates a top, close-up, exposed view of the access port according to an embodiment of the present invention.
Figure 10D:
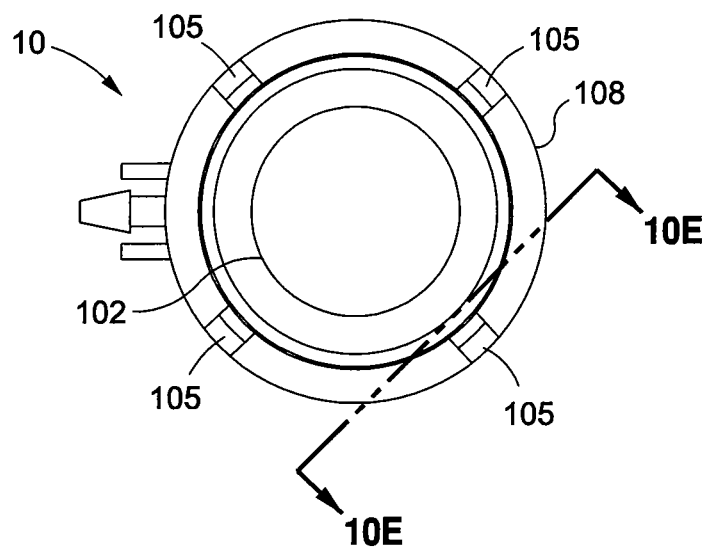
Figure 10E:
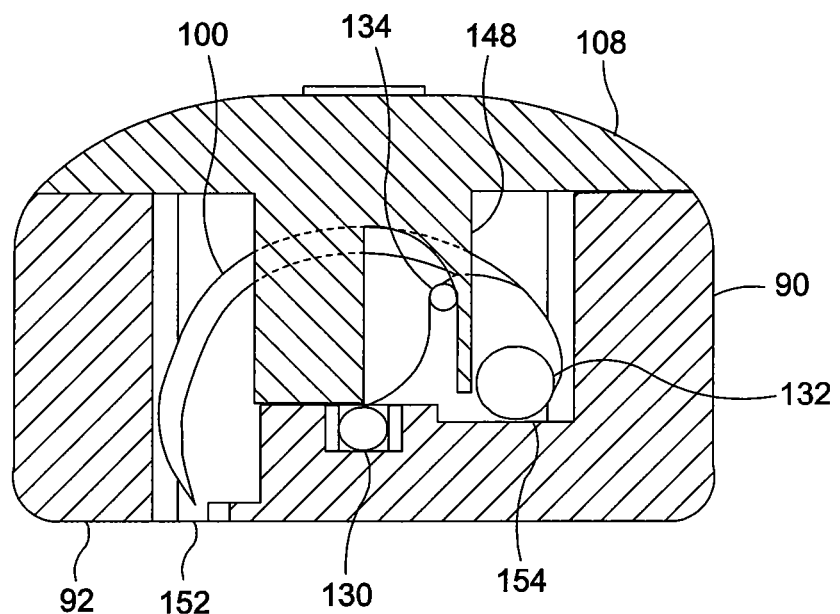
FIG. 10E illustrates a side, cross sectional view of the access port according to an embodiment of the present invention.

FIGS. 10C-10E illustrate two components of the actuator 108 that engage portions of the anchor assembly 100 shown in FIG. 10C. A cam surface 148 is positioned near the deploy pin 134, and an actuator surface 150 is positioned near the actuator pin 132. The cam surface 148 comprises a generally vertical surface of the actuator 108 having a curved portion located towards the top of the cam surface 148. The actuator surface 150 similarly comprises a vertical surface of the actuator 108, but having a curved portion located towards the bottom of the actuator surface 150. The cam surface 148 and actuator surface 150 may rotate along with the actuator 108. A portion of the cam surface 148 passes between the deploy pin 134 and the actuator pin 132. In addition, the actuator pin 132 rests against a locking surface 154. The locking surface 154 prevents the actuator 108 from rotating in a clockwise direction (with respect to the view shown in FIG. 10A) once the actuator pin 132 contacts the locking surface 154. FIG. 10E further illustrates that the position and structure of the cam surface 148 prevents the actuator 108 from rotating clockwise beyond the actuator pin 132, because a portion of the cam surface 148 contacts the actuator pin 132. The cam surface 148 and actuator surface 150 may either be integral with, or separate from the actuator 108.

During operation, the actuator 108 starts to rotate in a counter-clockwise manner (with respect to the view shown in FIG. 10A), and described in relation to FIGS. 15A-22B. It is noted that the actuator side cuts 105 shown in FIG. 10A will rotate with respect to the position of the tube connector 105. FIGS. 10A, 12A, and 13A approximately represent the rotation of the actuator side cuts 105 and the actuator 108. However, the positions of the actuator side cuts 105 shown in FIGS. 11B and 12D are not necessarily representative of the rotation of the actuator 108, although the cross section views in FIGS. 11C and 12E accurately represent the positions of the anchor assemblies 100 during deployment according to one embodiment of the present invention.

Figure 11A:
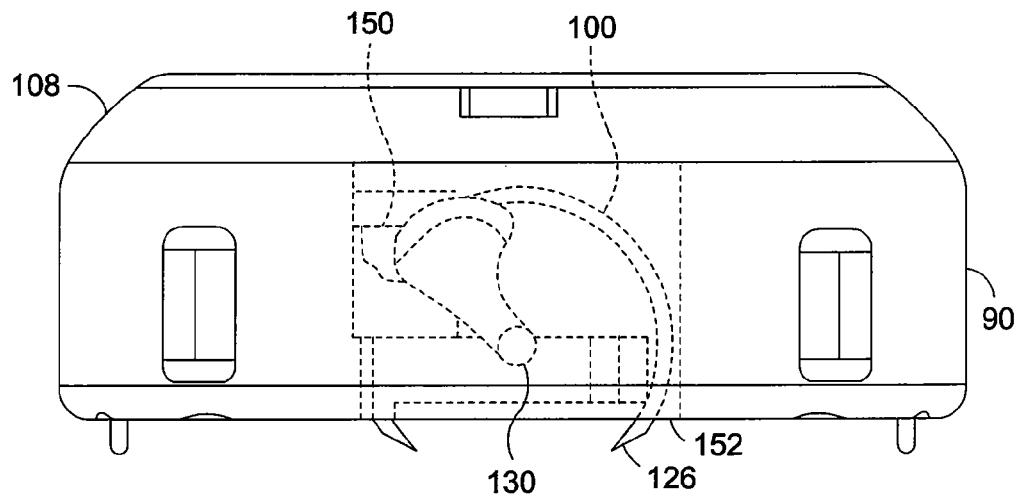
FIGS. 11A illustrates a side view of the access port according to an embodiment of the present invention.
Figure 11B:
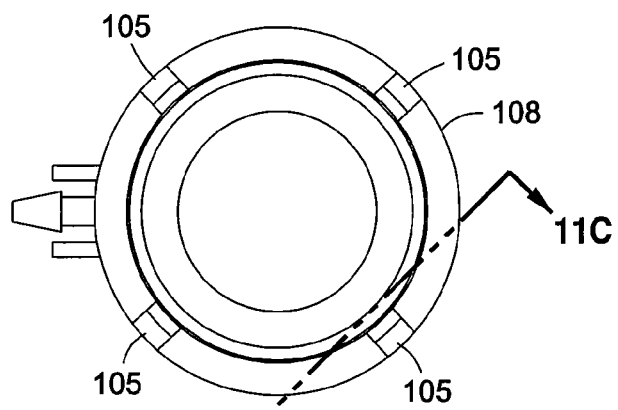
FIG. 11B illustrates a top view of the access port according to an embodiment of the present invention.
Figure 11C:
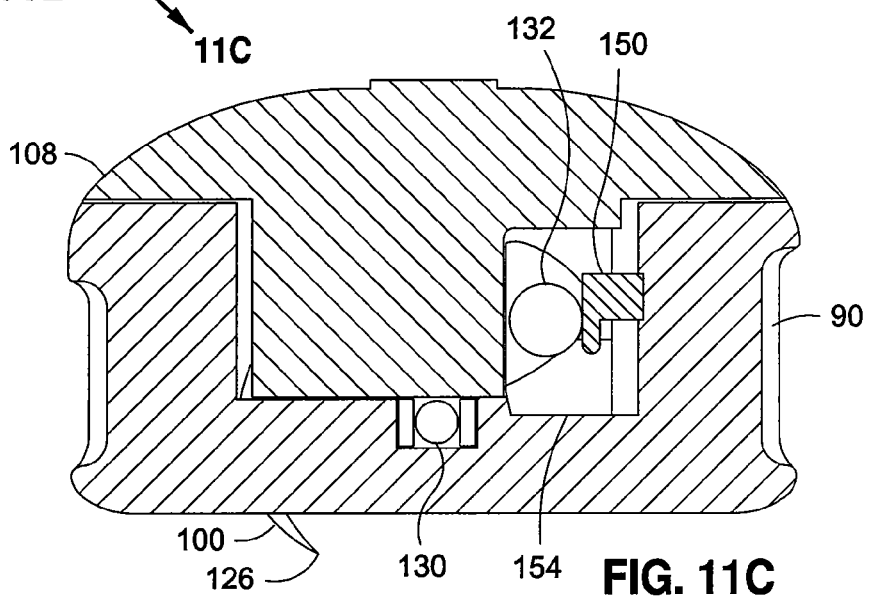
FIG. 11C illustrates a side, cross sectional view of the access port according to an embodiment of the present invention.
Figure 12A:
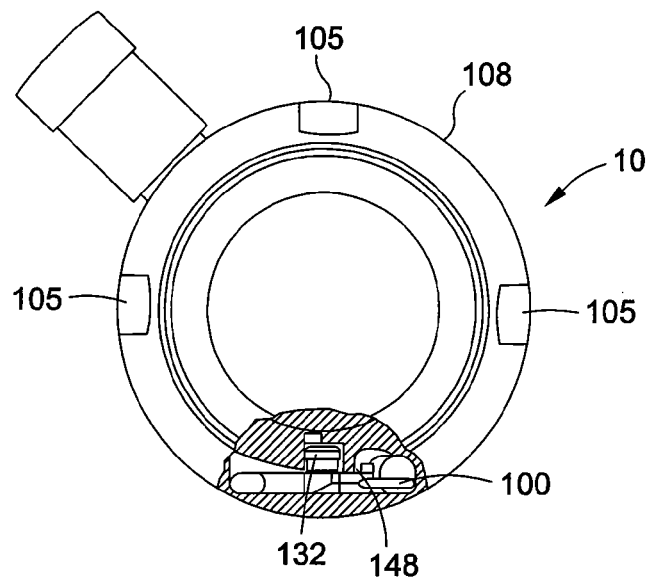
FIGS. 12A and 12D each illustrate a top view of the access port according to an embodiment of the present invention.
Figure 12B:
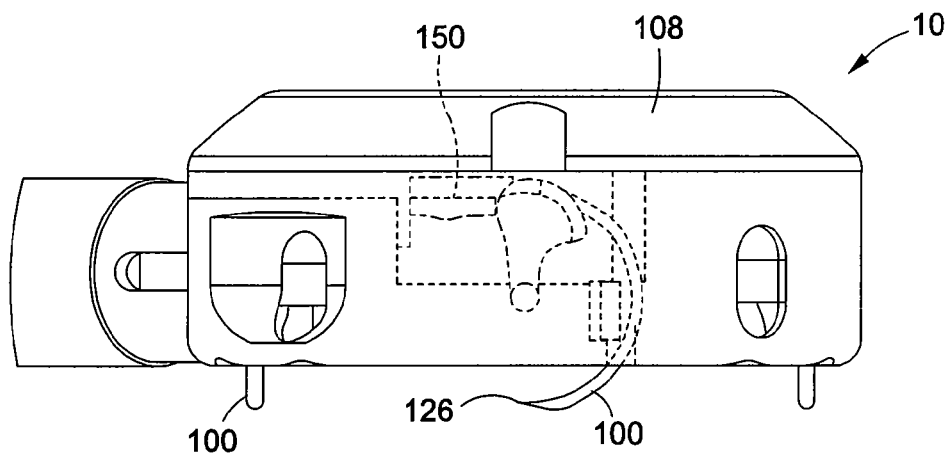
FIG. 12B illustrates a side view of the access port according to an embodiment of the present invention.
Figure 12C:
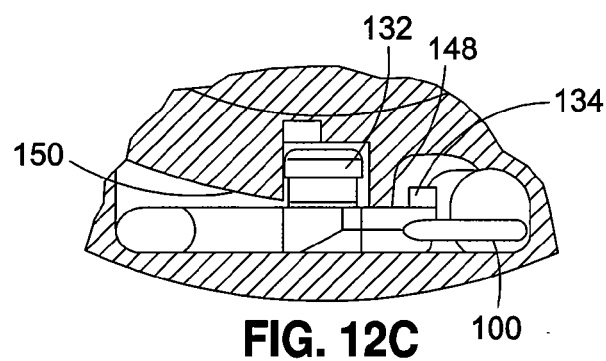
FIG. 12C illustrates a top, close-up, exposed view of the access port according to an embodiment of the present invention.
Figure 12D:
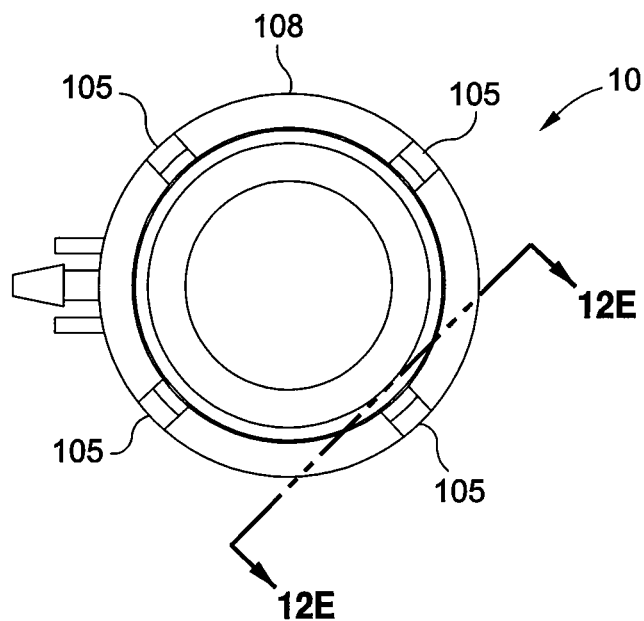

In FIGS. 11A-11C, during initial deployment, the cam surface 148 engages the deploy pin 134 and lifts the actuator pin 132 off the locking surface 154. The deploy pin 134 is positioned such that the motion of the cam surface 148 forces the deploy pin 134 in a direction tangential to a radius of rotation of the pivot axle 130. The tangential force rotates the anchor assembly 100 with respect to the position of the pivot axle 130 and lifts the actuator pin 132. As displayed in the configuration shown in FIG. 10E, if the actuator pin 132 was not initially lifted, and a force was applied to the actuator pin 132 by, for example, a cam surface, then the actuator surface 150 would not properly engage the actuator pin 132. Thus, the deploy pin 134 serves to initiate the movement of the actuator pin 132. The actuator pin 132 is preferably positioned at a maximum distance from the pivot axle 130 allowable, given the dimensions of the molded portion 128. The actuator pin 132 is positioned at a distant end of the molded portion 128 from the pivot axle 130 to maximize the driving torque to the anchor assembly 100. The position of the actuator pin 132 assures maximum torque is delivered throughout the majority of the deployment.

As shown in FIG. 11C, once the actuator pin 132 is lifted from the locking surface 154, the actuator surface 150 engages the actuator pin 132. At this point, the force transmitted by the actuator surface 150 is directed in a direction substantially tangential to a radius of rotation of the pivot axle 130, and is not substantially directed towards the pivot axle 130. Thus, the tangential force continues to rotate the anchor assembly 100 in the anchor assembly's 100 plane of rotation. FIGS. 11A-11C also illustrate the distal tip 126 has penetrated through the aperture 152. The apertures 152 are generally located in the base 92 of the access port 10.

FIGS. 12A-12E illustrate the anchor assembly 100 at a half deployment position, when the torque applied from the actuator surface 150 to a actuator pin 132 is at a maximum or near maximum. Thus, the actuator surface 150 is forcing the actuator pin 132 in a direction substantially parallel to a radius of rotation of the pivot axle 130. In other words, if a distance 162 is measured between the pivot axle 130 and the point of contact 164 between the actuator surface 150 and the actuator pin 132; and an angle 160 is formed between the distance 162 and the direction of the actuator surface's force 158, then the angle 160 at this point has a value near 90 degrees, or at a right angle with respect to the pivot axle 130. Thus, the torque is at a maximum, or near maximum at this point. A similar torque analysis could be performed for the configurations shown in FIGS. 10E, 11C, and 13E.

Figure 12E:
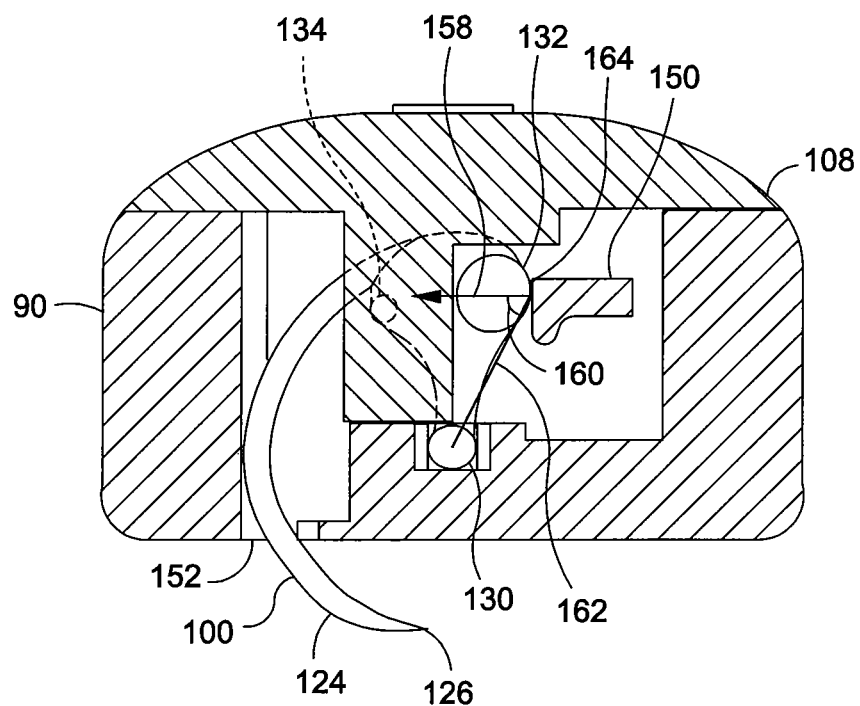
FIG. 12E illustrates a side, cross sectional view of the access port according to an embodiment of the present invention.
Figure 13A:
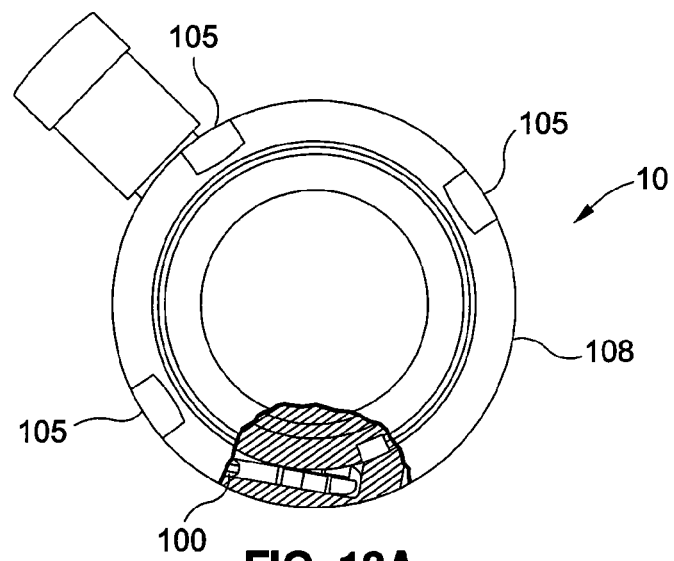
FIGS. 13A and 13D each illustrate a top view of the access port according to an embodiment of the present invention.
Figure 13B:
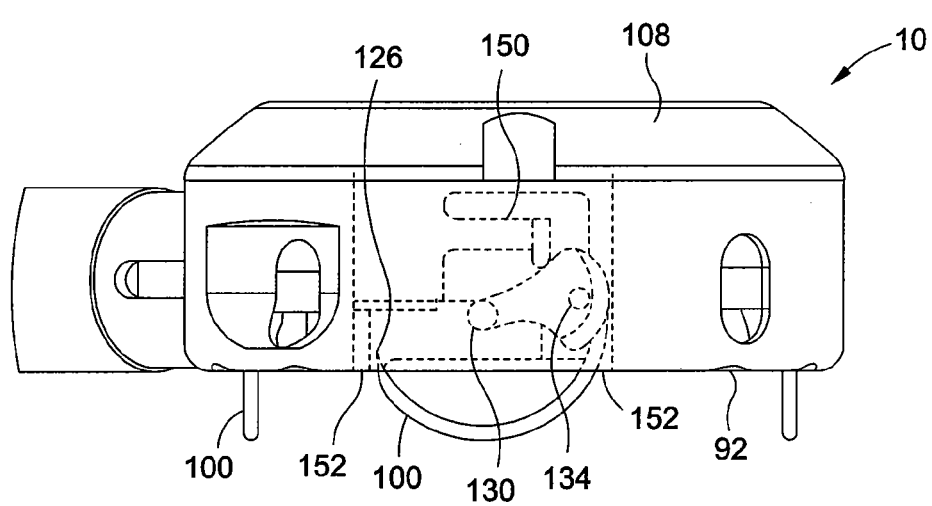
FIG. 13B illustrates a side view of the access port according to an embodiment of the present invention.
Figure 13C:
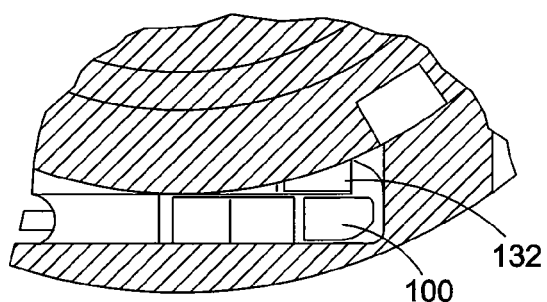
FIG. 13C illustrates a top, close-up, exposed view of the access port according to an embodiment of the present invention.
Figure 13D:
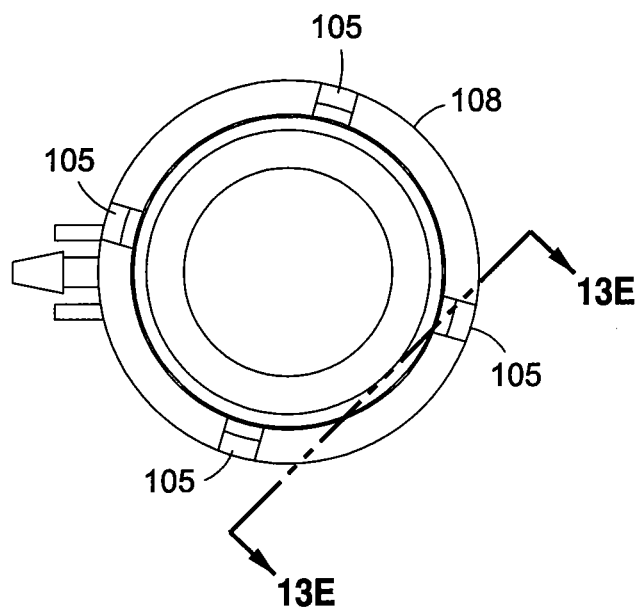

It is beneficial if the torque is at a maximum, or at a near maximum at the position shown in FIG. 12E, because the distal tip 126 and wire portion 124 will need to penetrate more tissue as the anchor assembly 100 continues to move from the retracted position to the deployed position. Thus, as the total friction and work increases, the actuator surface 150 will need to transfer energy more effectively to the anchor assembly 100.

Figure 13E:
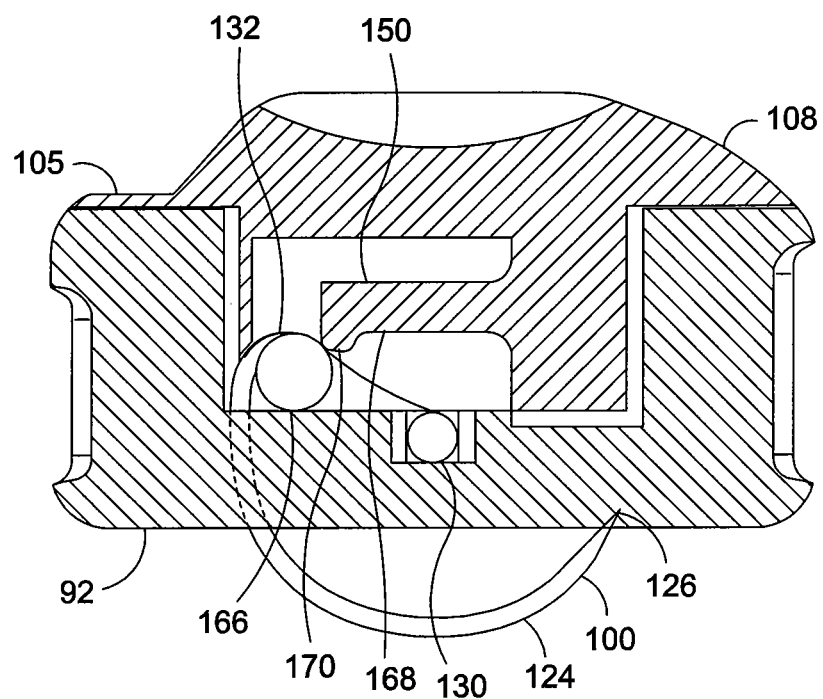
FIG. 13E illustrates a side, cross sectional view of the access port according to an embodiment of the present invention.

FIGS. 13A-13E illustrate the anchor assembly 100 fully rotated to a deployed position. The tip 126 has now extended into another aperture 152 located on the base 92 of the access port 10. In addition, as shown in FIG. 13E, the torque applied by the actuator surface 150 to the actuator pin 132 still remains high due to the geometry of the actuator surface 150 and the actuator pin 132. The actuator surface 150 and the actuator pin 132 both have rounded contact surfaces, which allow the actuator surface 150 to now drive the actuator pin 132 in a downward direction, still substantially tangential to a radius of rotation of the pivot axle 130. Thus, the torque remains at a maximum, or near maximum in this final deployed position. This large torque is especially desirable in the final deployed position because the tip 126 and the wire portion 124 have now passed through a large amount of tissue, as shown throughout the deployment stages in FIGS. 10A-13E. In addition, FIG. 13E illustrates the actuator pin 132 now is locked against locking surface 166, preventing further rotation of the anchor assembly 100. A horizontal portion 168 of the actuator surface 150 may additionally extend over the actuator pin 132, locking or trapping it in place against the locking surface 166. A small protruding step 170 of the actuator surface 150 may extend over the actuator pin 132, providing a snap lock during the last portion of the actuator 108 rotation. Trapping the actuator pin 132 between the horizontal portion 168 and the locking surface 166 of the actuator 108 and the housing 90 prevents the anchors 100 from being back-driven against the actuator 108.

To retract the anchor assembly 100 shown in FIGS. 10A-13E, the same process described is performed in reverse. However, in the reverse process, the cam surface 148 will now drive the actuator pin 132 in the opposite direction of rotation than that shown in FIGS. 10A-13E.

In the exemplary embodiments shown in FIGS. 10A-13E, it may be appreciated that the access port 10 has only two principle moving parts: the actuator 108 and the four anchor assemblies 100. Each of the anchor assemblies 100 functions identically as discussed above in FIGS. 10A-13E with respect to rotation of the actuator 108. The access port 10 is designed to maximize the transfer of force from the input torque of the actuator 108 to the output torque of the anchor assemblies 100. This is achieved, in part, by driving the anchor assemblies 100 as their farthest point (e.g., actuator pin 132) from their axes of rotation (e.g., pivot axle 130).

Each anchor assembly 100 may be made from stainless steel wire that is bent and sharpened. Wire is an efficient geometry to penetrate tissue, because of the minimal cross section, but it may be difficult to manufacture complex geometry with accurate bends. However, the wire used to form the anchor assemblies 100 requires only two simple bends which can be produced with accuracy due to the simplicity of manufacture.

Additional benefits of the anchor assembly 100 design include a greatly reduced force required to deploy the anchor assemblies 100, and that the anchors 100 do not require precision grinding for ample penetration into tissue. In addition, the design does not require high performance plastics such as PEEK. Furthermore, the manufacturing process is capable of 100% yield, the design does not require tight tolerances, there is a reduced high volume unit cost, the total number of components is low, and all complex parts are injection molded.

FIG. 14 illustrates an embodiment of the present invention including a pulpation ring 110 configured to prevent the fluid chamber 106 from leaking. The septum 102, as discussed above in relation to FIG. 6A, is positioned above the fluid chamber 106. The septum 102 is preferably composed of silicone, or another equivalent needle penetrable material. To access the fluid chamber 106, a physician will insert a syringe needle through a patient's skin and will penetrate the septum 102. The needle can then fill the fluid chamber 106 with fluid or remove fluid, to operate the gastric band 4, as shown in FIG. 1. However, if the syringe needle is inserted improperly, for example, near an interface between the septum 102 and the housing 90, then the septum 102 may no longer be able to seal the fluid chamber 106. Fluid may leak from the fluid chamber 106, eventually causing the gastric band 4 to fail. To remedy this problem, an upper rim 113 portion or top portion of the septum 102 may be housed within a ring shaped gap 172 formed between a bottom surface of the pulpation ring 110 and the housing 90. The ring shaped gap 172, as shown in FIG. 14, has a diameter (the length parallel to the base 92 of the access port 10 extending from one side of the gap 172 to the other side of the gap 172) greater than a diameter of the central cavity 104. In another words, the ring shaped gap 172 extends radially away from the center of the access port 10 further than the outward radial extent of the central cavity 104.

This upper rim 113 portion may be compressed between the pulpation ring 110 and the compression ring 107, to provide a tight seal for the fluid chamber 106. The septum 102 may include a top portion 175, a bottom portion 177, and the upper rim 113 portion positioned near the top portion 175. The upper rim 113 portion forms a concentric lip, or extended ridge, extending out further than the outer extent of the bottom portion 177 of the septum 102, or a local top portion 175 of the septum 102 not comprising the upper rim 113 portion. This upper rim 113 portion substantially encircles an outer circumference of the septum 102.

In addition, the pulpation ring 110 may include an inner annular ring portion 174 that extends in a direction towards the center of the top surface 176 of the septum 102. The pulpation ring 110 engages with a portion of the housing 90 including an inner circumference 179. The length of the annular ring portion 174 may be increased, to decrease the incident angle a syringe needle must travel at towards the septum 102, to contact the ring shaped gap 172. If the length of the annular ring portion 174 increases sufficiently, a syringe needle may need to pass nearly horizontally towards the ring shaped gap 172 to breach the compressed septum 102 and cause the fluid chamber 106 to leak. Furthermore, a height 178 of the ring shaped gap 172 may be sufficiently small such that a syringe needle can not penetrate the ring shaped cavity. For example, the height 178 may be smaller than 0.010 inches, leaving a small gap with a size narrower than the diameter of a conventional syringe needle. Thus, a conventional syringe needle could not penetrate the ring shaped gap 172. The ring shaped gap 172 helps to maintain the sealing integrity of the access port 10. The annular ring portion 174, and the ring shaped gap 172, may all have an annular, concentric shape conforming to the shape of the central cavity 104.

Figure 15A:
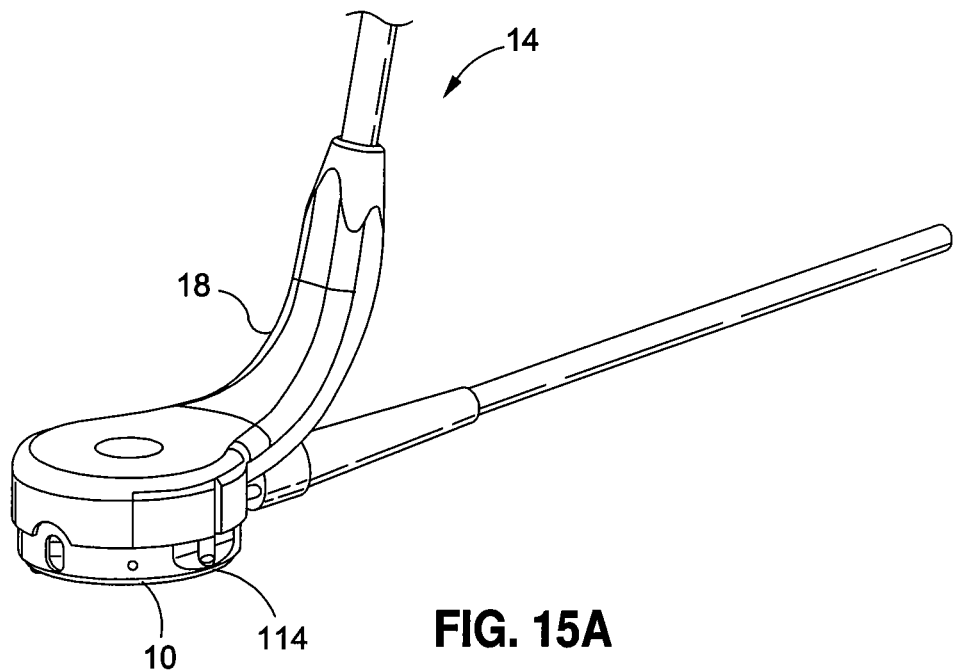
FIGS. 15A and 15B each illustrate a perspective view of the actuator head and access port according to an embodiment of the present invention.
Figure 15B:
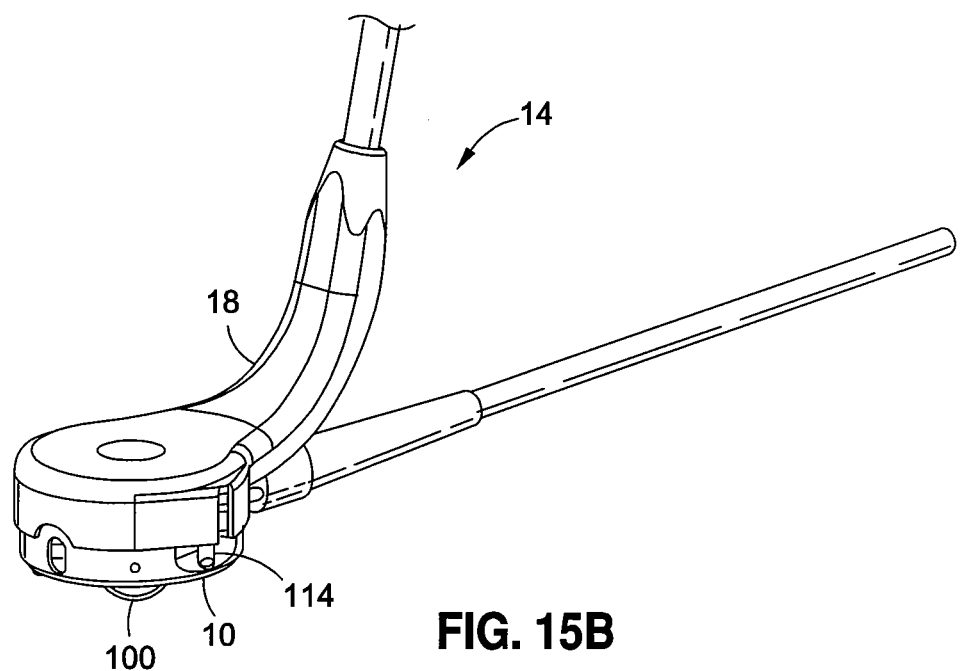
Figure 17A:
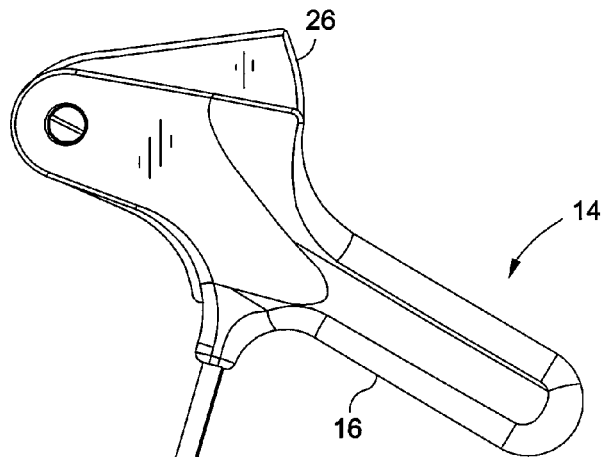
FIG. 17A illustrates a side view of the tool according to an embodiment of the present invention.
Figure 17C:
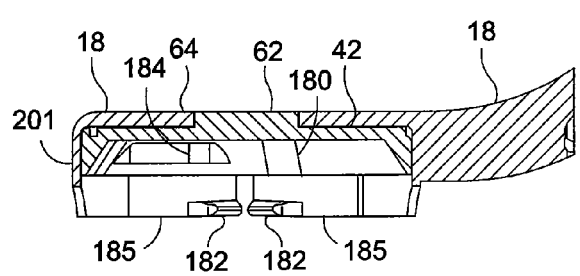
FIG. 17C illustrates a side, cross sectional view of the actuator head according to an embodiment of the present invention.
Figure 17D:
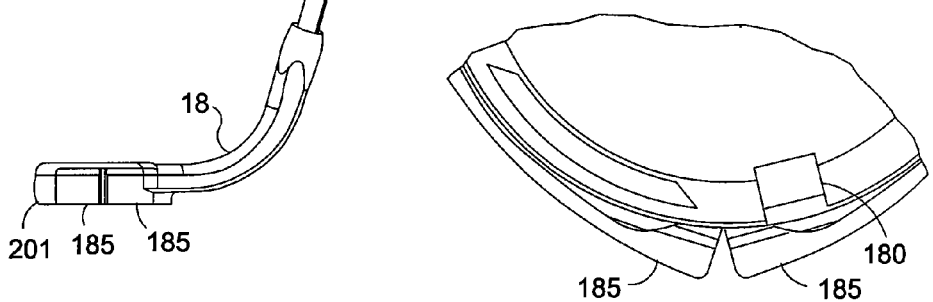
FIG. 17D illustrates a close-up bottom view of a portion of the actuator head according to an embodiment of the present invention.
Figure 17B:
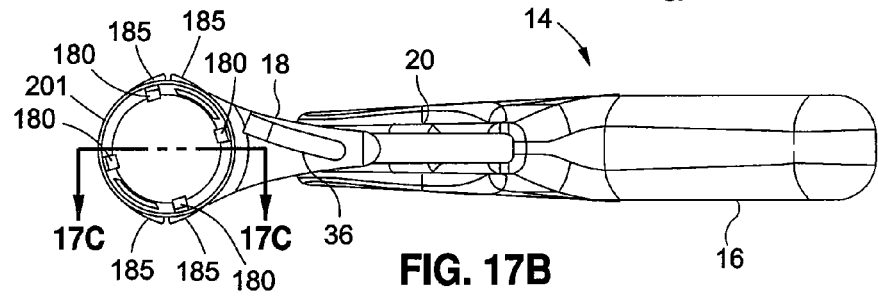
FIG. 17B illustrates a bottom view of the tool according to an embodiment of the present invention.

FIGS. 15A and 15B illustrate the tool 14 being used to deploy the access port 10. The tool 14 is designed to minimize the linkage between the trigger 26 (shown in FIG. 3B) and the actuator cap 42 (shown in FIG. 3B), with the actuator cap 42 applying a torque to the actuator 108 (shown in 8A-8C) to deploy and retract the anchor assemblies 100. The linkage is further designed to provide the user maximum tactile response while deploying and retrieving an access port 10. The basic functionality involves loading the access port 10 into the actuator head 18 of the tool 14. Once the access port 10 is loaded, the user pulls the trigger 26 to deploy the anchors 100 and then reverses the trigger 26 to retract the anchors 100. The deploying and reversing process has been discussed above in relation to FIGS. 10A-13E.

The actuator head 18 is configured to mate with the access port. The actuator head 18 generally has a cylindrical shape conforming to a cylindrical shape of the access port 10, and receiving the access port 10. Retaining clips (shown in FIG. 16C) located on the sides of the actuator head 18 engage with the side cuts 114 on the access port 10. The retaining clips grip the access port 10 until the user deploys the access port 10. FIG. 15B illustrates the access port 10 in a deployed state, where the anchor assemblies 100 extend outward from the anchor port 10 to the deployed position. The access port 10 then disengages from the retaining clips, and the physician may remove the tool 14 from the access port 10.

FIGS. 16A-16D illustrate the tool 14 in the retracted or undeployed state. In addition, no access port 10 is shown engaged with the actuator head 18. As shown in FIG. 16C, the actuator head 18 includes retaining clips 182 that grip the side cuts 114 on the access port 10 (shown in FIGS. 15A and 15B). The retaining clips 182 are fixed to flexible sidewalls 185 that are capable of rotating out away from the actuator head 18. The flexible sidewalls 185 comprise a skirt portion 201 of the actuator head 18 that extends around an outer circumference of the access port 10. The skirt portion 201 helps to hold and retain the access port 10.

In addition, a set of actuator features 180, shown in FIGS. 16B-D, are formed as part of the actuator cap 42, which is rotatably coupled to the actuator head 18. The shape and position of the actuator features 180 correspond to the actuator side cuts 105, shown in FIGS. 8A-8C. The actuator features 180 interface with the actuator side cuts 105 to rotate the actuator 108 and to correspondingly deploy the anchor assemblies 100.

The actuator head 18 additionally includes cam protrusions 184, shown in FIGS. 16C and 16D, that are positioned around the periphery of the actuator head 18 and are coupled to the retaining clips 182. The cam protrusions 184 may be integral with the flexible sidewalls 185. The cam protrusions 184 extend toward the center of the actuator head 18. The cam protrusions 184 respond to the rotation of the actuator cap 54, and are displaced when the actuator features 180 rotate when the tool 14 is deployed. The displacement of the cam protrusions 184 causes the flexible sidewalls 185 to be displaced away from the actuator head 18. Thus, the cam protrusions 184 cause the retaining clips 182 to disengage from the side cuts 114 on the access port 10.

In the retracted, or undeployed state shown in FIGS. 16A-16D, the four actuator features 180 align with the actuator side cuts 105 when the tool 14 is placed over the access port 10. When the tool 14 is placed over the access port 10, the retaining clips 182 spring open and close into the side cuts 114 of the access port 10 to retain it.

FIGS. 17A-17D illustrate the tool 14 in the deployed state. In this position, the user has pressed the trigger 26, which has caused the actuator cap 42 to rotate. Pressing the trigger 26 pulls on the actuator cable assembly 40 (shown in FIG. 3B), which has been wrapped around a portion of the actuator cap 42. The cam protrusions 184 have therefore now been displaced and the retaining clips 182 extend outwards to release from the side cuts 114 of an access port 10 (shown in FIGS. 15A and 15B).

The tool 14 can then be reapplied to the access port 10 in either the retracted or deployed state. In the deployed state the actuator head 18 is placed in contact with the access port 10 and the trigger 26 is reversed to its retracted state. This operation retracts the anchor assemblies 100 and the retainer clips 182, which capture the access port 10 for removal. The access port 10 can also be removed by the tool 14 when it is in the retracted state. By pushing the actuator head 18 onto the access port 10 the retainer clips 182 will spring out, allowing the actuator cap 54 to contact the access port actuator 108. Because the actuator features 180 in the actuator cap 42 are not longer aligned with the actuator side cuts 105 in the actuator 108, the retainer clips 182 cannot engage the side cut 114 of the access port 10. However, pulling the trigger 26 to the deployed state will rotate the actuator cap 42 until it aligns with the access port actuator 108. At the end of the trigger pull, the actuator features 180 in the actuator cap 42 will engage the actuator side cuts 105. Reversing the trigger 26 will then retract the anchors 100 and capture the access port 10 for removal.

Figure 18A:
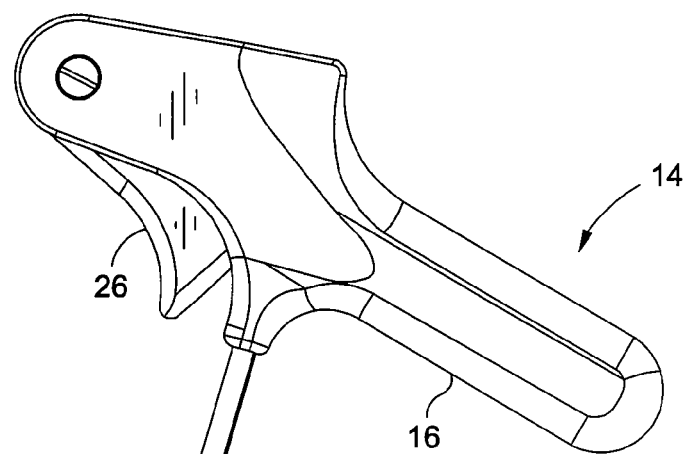
FIGS. 18A and 18C each illustrate a side view of the system according to an embodiment of the present invention.
Figure 18B:
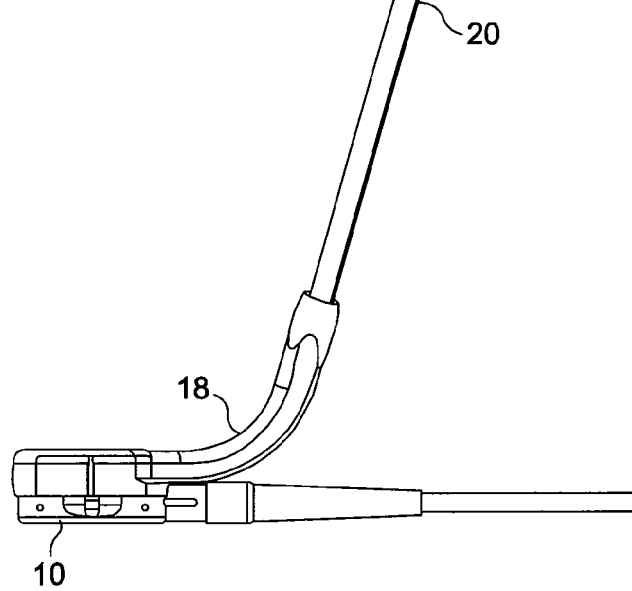
FIGS. 18B and 18D each illustrate a bottom view of the system according to an embodiment of the present invention.
Figure 18B:
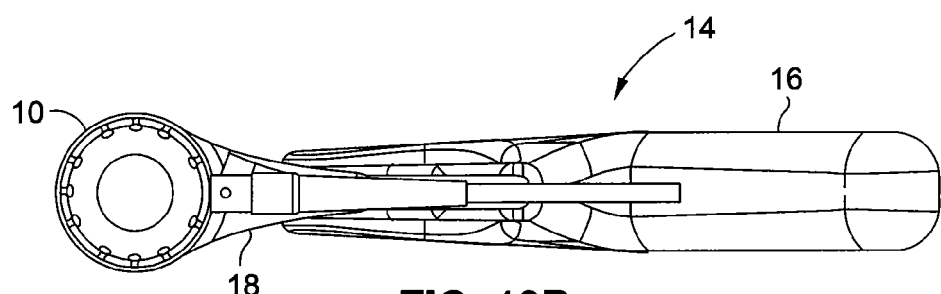
Figure 18C:
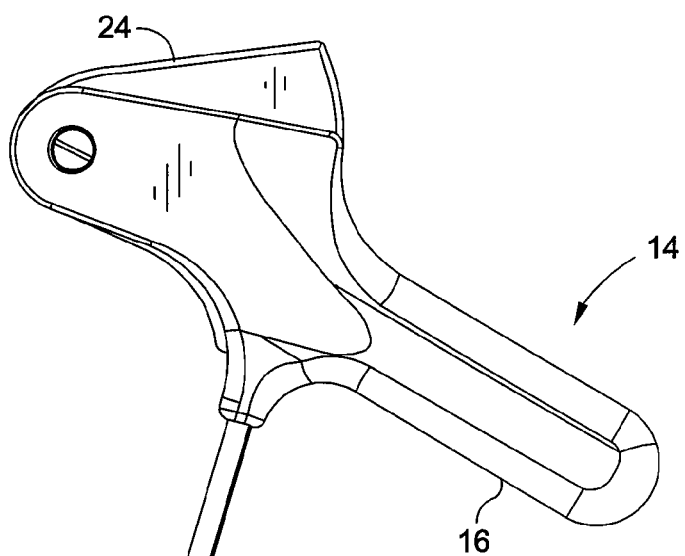
Figure 18C:
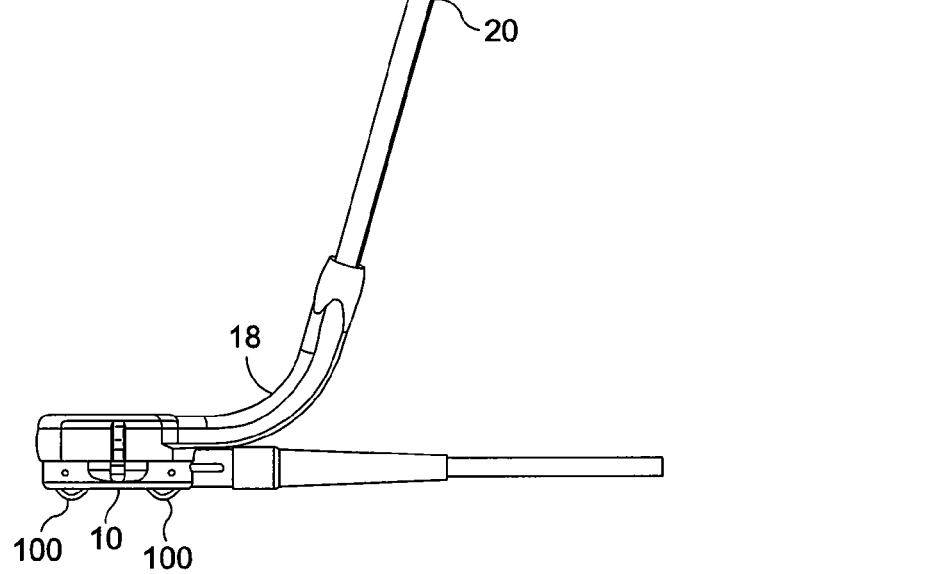
Figure 18D:
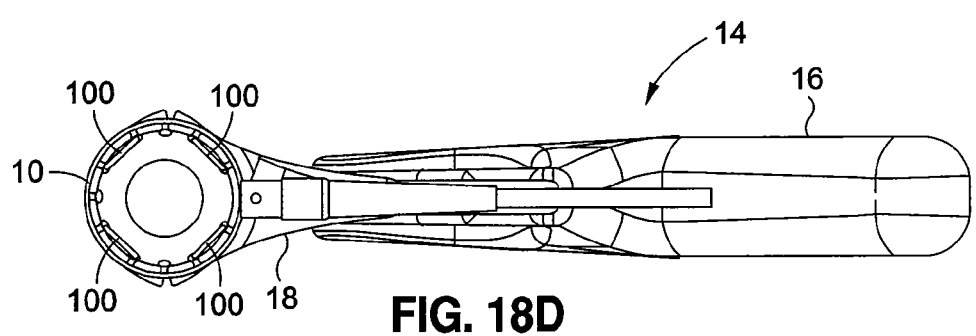

FIGS. 18A and 18B illustrate the access port 10 engaged with the tool 14 in the retracted position. FIGS. 18C and 18D illustrate the access port 10 engaged with the tool 14 in the deployed position. In FIG. 18D, the anchors 100 are displayed extended from the access port 10.

FIGS. 19A-19D are substantially similar to the embodiment shown in FIGS. 16A-16D. However, in the embodiment shown in FIGS. 19A-19D, the actuator head 18 has a lower profile, allowing for easier horizontal and vertical engagement with the access port 10. A front portion, or a half portion of the skirt portion 201 of actuator head 18 has been removed, increasing the total engagement area. Only one flexible sidewall 185 on each side of the actuator head 18 is used. The tool 14 may now be horizontally slid to capture the access port 10. The shape of the actuator head 18 may also be considered a semi-circular shape, as a skirt portion 201 of the actuator head 18 does not extend entirely around the actuator head 18. The operation shown in FIGS. 20A-20D substantially mirrors the operation of the embodiment shown in FIGS. 17A-17D.

Figure 21A:
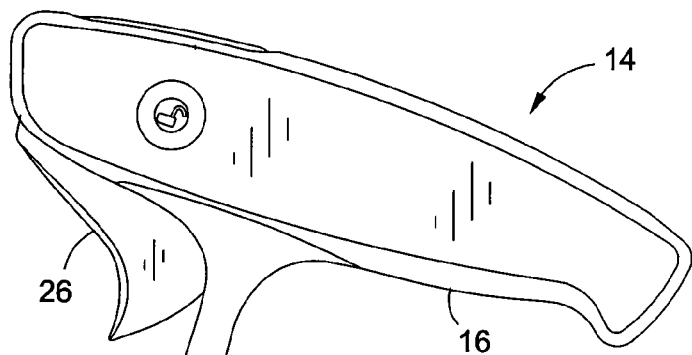
FIGS. 21A and 22A each illustrate a side view of the system according to an embodiment of the present invention.
Figure 21B:
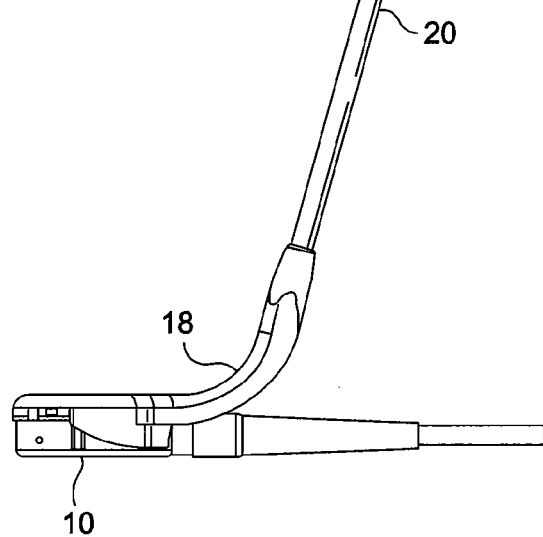
FIGS. 21B and 22B each illustrate a bottom view of the system according to an embodiment of the present invention.
Figure 21B:
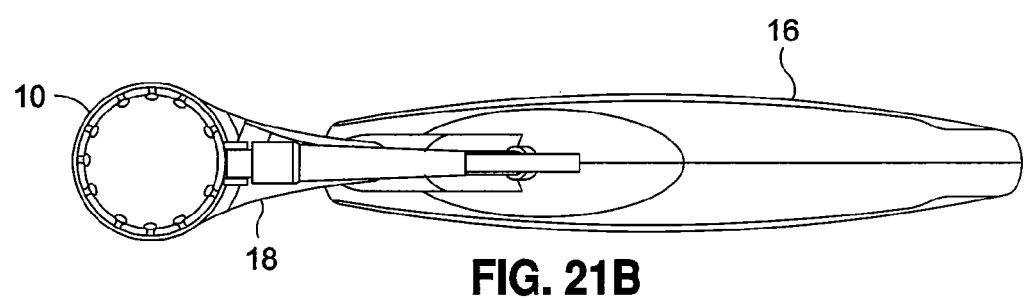
Figure 22A:
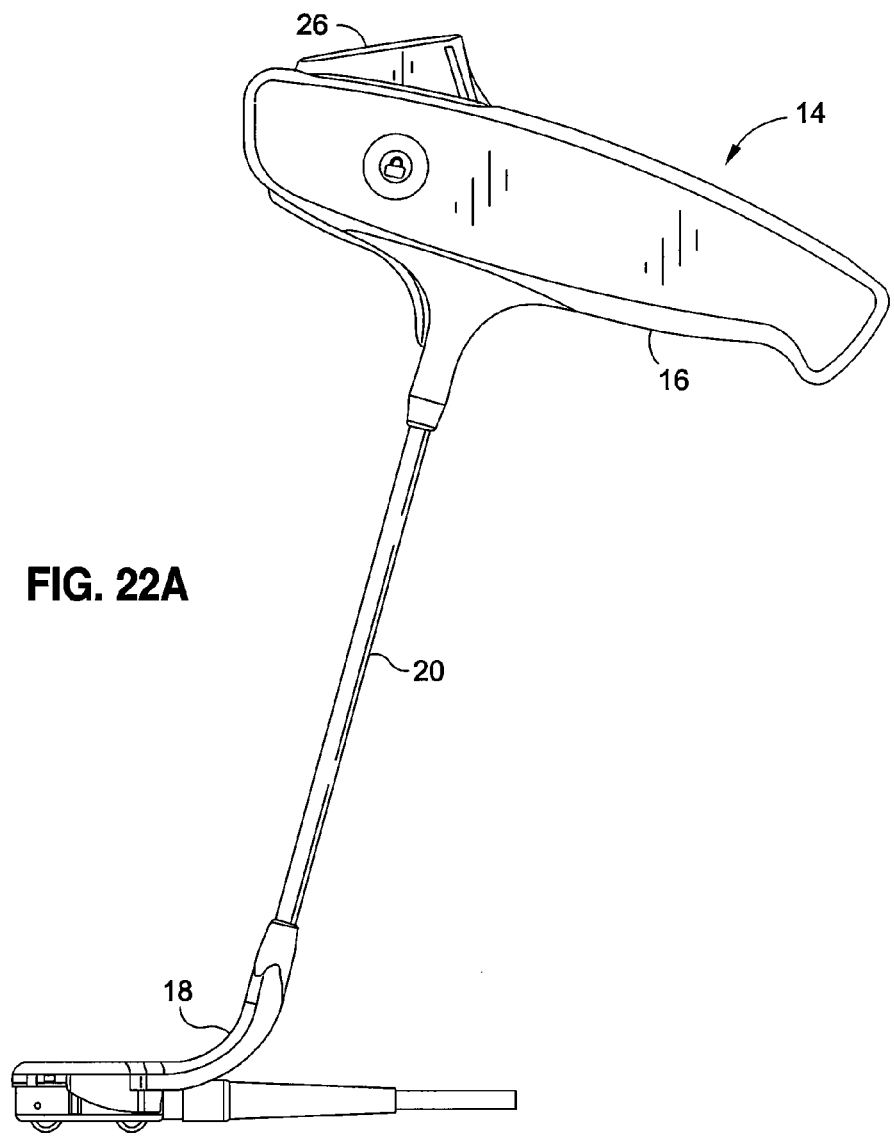
Figure 22B:
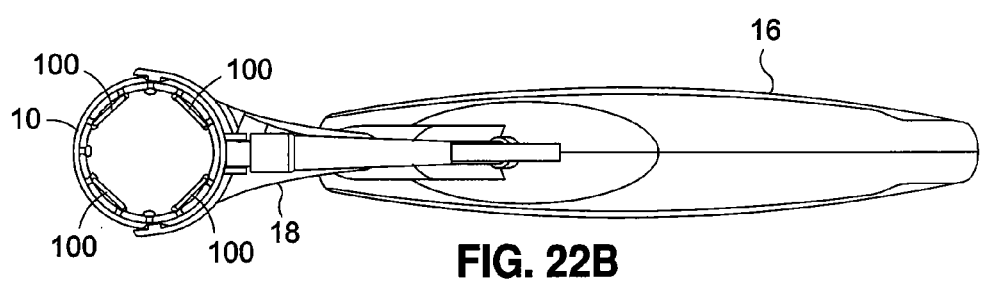

FIGS. 21A and 21B illustrate the embodiment of the tool 14 shown in FIGS. 19A-20D engaged with an access port 10. The actuator head 18 in this embodiment similarly displays the exposed front portion, or skirt portion 201 of the access port 10. As discussed above, the exposed or open portion of the actuator head 18 may allow for easier retrieval or placement of the access port 10. FIGS. 22A and 22B illustrate the embodiment of the tool 14 shown in FIGS. 19A-20D in the deployed position. In FIG. 22B, the anchor assemblies visibly extend from the access port 10.

FIGS. 23 and 24 illustrate a feature of the present invention including multiple orientations of the access port 10 with respect to the position of the tool 14 or handle 16. As discussed above with regard to FIGS. 15A-17D, the actuator head 18 need only engage side cuts 114 of the access port 10 to retain the access port 10. In addition, the actuator cap 42 need only mate with the actuator features 180 with the actuator side cuts 105. Because the access port 10 and the actuator head 18 include generally symmetric features, the port side cuts 114 and actuator side cuts 105 may engaged with the tool 14 in varied positions. The skirt portion 201 (discussed above in relation to FIGS. 16A and 19A) may be shaped to allow an access port 10 to engage the actuator head 18 in multiple orientations. In the embodiment shown in FIGS. 23 and 24, the access port 10 is shown in two opposite positions with respect to the tool, yet extending parallel to an orientation of the actuator head 18. However, it is also contemplated that the access port 10 may also be positioned in directions perpendicular to the orientation of the actuator head 18. The variety of orientations generally improves the useful positions of the tool 14 and access port 10, similar to benefits of the pivotal actuator head 18, discussed above in relation to FIGS. 4A and 4B.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A system for attaching a fluid access port to a patient, the system comprising:
   an access port including a plurality of rotatable anchor assemblies, each anchor assembly comprising a wire portion and a molded portion secured to the wire portion; and
   a tool configured to facilitate attachment of the access port to the patient;
      wherein the wire portion is made of metal and the molded portion is made of plastic.

2. The system of claim 1 wherein the molded portion is molded to the wire portion.

3. The system of claim 1 wherein the molded portion is overmolded to the wire portion.

4. The system of claim 1 wherein the wire portion has a proximal portion and distal portion, the distal portion including a tip structured to penetrate and engage tissue, the molded portion molded to the proximal portion of the wire portion.

5. The system of claim 1 wherein the molded portion includes a pivot axle having an axis substantially perpendicular to a plane of rotation of the wire portion.

6. The system of claim 1 wherein the molded portion includes an actuator pin and a deploy pin spaced apart from the actuator pin.

7. An implantable access port for providing fluid access to a patient, the access port comprising:
   a septum;
   a housing secured to the septum; and
   a plurality of rotatable anchor assemblies fixed to the housing, each anchor assembly comprising a wire portion and a molded portion secured to the wire portion;
      wherein the wire portion is made of metal and the molded portion is made of plastic.

8. The access port of claim 7 wherein the molded portion is molded to the wire portion.

9. The access port of claim 7 wherein the molded portion is overmolded to the wire portion.

10. The access port of claim 7 wherein the wire portion has a proximal portion and distal portion, the distal portion including a tip structured to penetrate and engage tissue, the molded portion molded to the proximal portion of the wire portion.

11. The access port of claim 7 wherein the molded portion includes a pivot axle having an axis substantially perpendicular to a plane of rotation of the wire portion.

12. The access port of claim 7 wherein the molded portion includes an actuator pin and a deploy pin spaced apart from the actuator pin.

13. A tool for securing a fluid access port to a patient, the assembly comprising:
   a handle having a trigger; and
   an actuator head coupled to the trigger and configured to removably engage and deploy an access port;
   the actuator head being pivotal with respect to the handle;
   the tool further comprising an extension tube coupling the actuator head to the handle, a length of the extension tube defining an axis of rotation, the actuator head being pivotal about the axis of rotation,
   wherein the actuator head is configured to pivot 360 degrees around the axis of rotation.

14. The tool of claim 13 wherein the actuator head is configured to removably engage an access port in more than one orientation.

15. The tool of claim 13 further comprising an actuator cable assembly having a proximal portion coupled to the handle and a distal portion coupled to the actuator head, and a ball fixed to the proximal portion and connecting the proximal portion to the handle, the ball enabling the actuator head to pivot with respect to the handle.

16. A system for attaching a fluid access port to a patient, the system comprising:
   an access port comprising a septum, a housing secured to the septum, and a plurality of rotatable anchor assemblies fixed to the housing, each anchor assembly comprising a wire portion and a molded portion overmolded to the wire portion; and a tool configured to facilitate attachment of the access port to a patient, the tool comprising a handle having a trigger, and an actuator head coupled to the handle and configured to removably engage and deploy an access port, the actuator head being pivotal with respect to the handle.

17. The system of claim 16 wherein the actuator head is configured to removably engage an access port in more than one orientation.

18. The system of claim 16 further comprising a pivot device pivotally coupling the actuator head to the handle.

19. The system of claim 16 further comprising an extension tube coupling the actuator head to the handle, a length of the extension tube defining an axis of rotation, the actuator head being pivotal about the axis of rotation.

20. The system of claim 19 wherein the actuator head is configured to pivot 360 degrees around the axis of rotation.

21. The system of claim 16 further comprising an actuator cable assembly having a proximal portion coupled to the handle and a distal portion coupled to the actuator head, and a ball fixed to the proximal portion and connecting the proximal portion to the handle, the ball enabling the actuator head to pivot with respect to the handle.

22. An implantable access port for providing fluid access to a patient, the access port comprising:
   a septum;
   a housing secured to the septum and including a base substantially opposing the septum, the base having a bottom surface; and
   a mesh member having a top surface and a bottom surface, the top surface of the mesh member secured to the bottom surface of the base for encouraging tissue ingrowth when the access port is implanted in a patient;
      wherein the mesh member includes a portion extending beyond the base.

23. The access port of claim 22 wherein the mesh member does not substantially extend beyond the base.

24. The access port of claim 22 wherein the mesh member substantially circumscribes the base.

25. The access port of claim 22 wherein the mesh member extends substantially parallel to the base.

26. The access port of claim 22 wherein the mesh member is welded or adhered to the bottom surface of the base.

27. The access port of claim 22 further comprising a ring having a top surface and a bottom surface, the top surface of the ring removably or permanently fixed to the bottom surface of the base, the bottom surface of the ring firmly fixed to the mesh member.

28. The access port of claim 22 further comprising a ring having a top surface and a bottom surface, the top surface of the ring removably or permanently fixed to the bottom surface of the base, a portion of the mesh member being firmly or loosely sandwiched between the top surface of the ring and a bottom surface of the base.

29. The access port of claim 22 wherein the mesh member is integrally molded as part of the base of the access port.

30. The access port of claim 22 wherein the mesh member is made of a material selected from a group consisting of a bioresorbable, a non-resorbable, and combinations therein.

31. An implantable access port for providing fluid access to a patient, the access port comprising:
   a septum;
   a housing secured to the septum and including a base substantially opposing the septum, the base having a bottom surface;
   a plurality of rotatable anchor assemblies fixed to the housing; and
   a coating of a bioresorbable material covering a portion of the bottom surface of the base;
      wherein the coating has an even thickness.

32. The access port of claim 31 wherein the coating has a thickness in a range between 0.001 inches and 0.25 inches.

33. The access port of claim 31 wherein the coating is deposited to the base by a process selected from a group consisting of a spraying process, a dipping process, a molding process, a wiping process, and combinations therein.

34. An implantable access port for providing fluid access to a patient, the access port comprising:
   a septum;
   a housing secured to the septum and including a base substantially opposing the septum, the base having a bottom surface, a portion of the bottom surface of the base being made of a bioresorbable material; and
   a plurality of rotatable anchor assemblies fixed to the housing;
      wherein the entirety of the bottom surface of the base is made of a bioresorbable material.

35. The access port of claim 34 wherein the portion of the bottom surface of the base being made of a bioresorbable material is formed by a process selected from a group consisting of a molding process, a forming process, a stamping process, and combinations therein.

36. An implantable access port for providing fluid access to a patient, the access port comprising:
   a housing defining a central cavity;
   a pulpation ring engaged with the housing, the engagement of the pulpation ring and the housing defining a ring shaped gap having a diameter greater than a diameter of the central cavity;
   a septum having a top portion, a bottom portion, and a rim located near the top portion, the bottom portion of the septum positioned in the central cavity, the rim of the septum positioned in the ring shaped gap; and
   a plurality of rotatable anchor assemblies fixed to the housing;
      comprising a compression ring positioned within the central cavity.

37. The access port of claim 35 wherein the rim of the septum is compressed between the pulpation ring and the compression ring.

38. The access port of claim 35 wherein the ring shaped gap has a height of no more than 0.010 inches.

* * * * *